US012741026B2

(12) United States Patent
Turnquist et al.

(10) Patent No.: US 12,741,026 B2

(45) Date of Patent: Sep. 22, 2026

(54) MICROPARTICLE-ASSISTED Treg THERAPY FOR TREATMENT OF TISSUE INJURY AND FIBROSIS

(71) Applicant: University of Pittsburgh—Of the Commonwealth System of Higher Education, Pittsburgh, PA (US)

(72) Inventors: Heth Turnquist, Pittsburgh, PA (US); Stephen F. Badylak, West Lafayette, IN (US); George S. Hussey, Cranberry Township, PA (US); Angus W. Thomson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 903 days.

(21) Appl. No.: 17/920,290

(22) PCT Filed: Apr. 23, 2021

(86) PCT No.: PCT/US2021/028871

§ 371 (c)(1),
(2) Date: Oct. 20, 2022

(87) PCT Pub. No.: WO2021/217018

PCT Pub. Date: Oct. 28, 2021

(65) Prior Publication Data

US 2023/0210898 A1 Jul. 6, 2023

Related U.S. Application Data

(60) Provisional application No. 63/015,038, filed on Apr. 24, 2020.

(51) Int. Cl.

*A61K 35/17* (2025.01)
*A61K 40/11* (2025.01)

(Continued)

(52) U.S. Cl.

CPC ............ *A61K 40/418* (2025.01); *A61K 40/11* (2025.01); *A61K 40/22* (2025.01); *A61K 40/416* (2025.01); *A61P 37/06* (2018.01); *A61K 2239/38* (2023.05)

(58) Field of Classification Search

CPC ...... A61K 40/418; A61K 40/11; A61K 40/22; A61K 40/416; A61K 2239/38; A61K 9/08; A61K 9/0019; A61P 37/06; A61P 29/00

See application file for complete search history.

(56) References Cited

U.S. PATENT DOCUMENTS 4,902,508 A 2/1990 Badylak et al.
4,956,178 A 9/1990 Badylak et al.

(Continued)

FOREIGN PATENT DOCUMENTS

WO 0297070 A1 12/2002
WO 2005079844 A2 9/2005

(Continued)

OTHER PUBLICATIONS

Matta "Expansion of Regulatory T Cells in Vitro and In Vivo by IL-33" Chapter 3 of Suppression and Regulation of Immune Responses Chapter 3 of Suppression and Regulation of Immune Responses (Year: 2016).*

(Continued)

*Primary Examiner* — Tracy Vivlemore
*Assistant Examiner* — Lauren K Van Buren
(74) *Attorney, Agent, or Firm* — The Webb Law Firm

(57) ABSTRACT

Provided herein are transplantation methods and methods of treating an inflammatory condition, ischemia reperfusion injury, infection, or a wound in a patient, comprising administering isolated IL-33 matrix-bound vesicles to the patient, as well as in vitro-expanded Treg cells. Also provided is a kit (Continued)

comprising IL-33 matrix-bound vesicles and in vitro-expanded Treg cells.

8 Claims, 17 Drawing Sheets

Specification includes a Sequence Listing.

(51) Int. Cl.
*A61K 40/22* (2025.01)
*A61K 40/41* (2025.01)
*A61P 37/06* (2006.01)

(56) References Cited

U.S. PATENT DOCUMENTS

| | | | | |
|---|---|---|---|---|
| 5,281,422 | A | 1/1994 | Badylak et al. | |
| 5,352,463 | A | 10/1994 | Badylak et al. | |
| 5,372,821 | A | 12/1994 | Badylak et al. | |
| 5,554,389 | A | 9/1996 | Badylak et al. | |
| 5,573,784 | A | 11/1996 | Badylak et al. | |
| 5,645,860 | A | 7/1997 | Knapp, Jr. et al. | |
| 5,753,267 | A | 5/1998 | Badylak et al. | |
| 5,762,966 | A | 6/1998 | Knapp, Jr. et al. | |
| 5,771,969 | A | 6/1998 | Garay | |
| 5,866,414 | A | 2/1999 | Badylak et al. | |
| 6,099,567 | A | 8/2000 | Badylak et al. | |
| 6,485,723 | B1 | 11/2002 | Badylak et al. | |
| 6,576,265 | B1 | 6/2003 | Spievack | |
| 6,579,538 | B1 | 6/2003 | Spievack | |
| 6,696,270 | B2 | 2/2004 | Badylak et al. | |
| 6,746,670 | B2 | 6/2004 | Levings et al. | |
| 6,783,776 | B2 | 8/2004 | Spievack | |
| 6,793,939 | B2 | 9/2004 | Badylak | |
| 6,849,273 | B2 | 2/2005 | Spievack | |
| 6,852,339 | B2 | 2/2005 | Spievack | |
| 6,861,074 | B2 | 3/2005 | Spievack | |
| 6,887,495 | B2 | 5/2005 | Spievack | |
| 6,890,562 | B2 | 5/2005 | Spievack | |
| 6,890,563 | B2 | 5/2005 | Spievack | |
| 6,890,564 | B2 | 5/2005 | Spievack | |
| 6,893,666 | B2 | 5/2005 | Spievack | |
| 9,277,999 | B2 | 3/2016 | Badylak et al. | |
| 2009/0010950 | A1 | 1/2009 | Roncarolo et al. | |
| 2012/0076831 | A1 | 3/2012 | Miller et al. | |
| 2015/0079026 | A1 | 3/2015 | Little et al. | |
| 2018/0139937 | A1* | 5/2018 | Paczesny ............. | C12N 5/0636 |
| 2021/0106526 | A1 | 4/2021 | Badylak et al. | |

FOREIGN PATENT DOCUMENTS

| | | | |
|---|---|---|---|
| WO | 2017151862 | A1 | 9/2017 |
| WO | 2019213482 | A1 | 11/2019 |

OTHER PUBLICATIONS

Brunner et al., “Interleukin-33 prolongs allograft survival during chronic cardiac rejection”, Transplant International, 2011, pp. 1027-1039, vol. 24:10.
Fisher et al., “In situ recruitment of regulatory T cells promotes donor-specific tolerance in vascularized composite allotransplantation”, Sci Adv., 2020, p. eaax8429, vol. 6:11.
Fisher et al., “Treg-inducing microparticles promote donor-specific tolerance in experimental vascularized composite allotransplantation”, Proc Natl Acad Sci USA., 2019, pp. 25784-25789, vol. 116:51.
Genbank® NCBO Accession No. NP_001186569, Version No. NP_001186569, “interleukin-33 isoform b [*Homo sapiens*]”, available at https://www.ncbi.nlm.nih.gov/protein/NP_001186569.1.
Genbank® NCBI Accession No. NP 001186570, Version No. NP_001186570.1, “interleukin-33 isoform c [*Homo sapiens*]”, available at https://www.ncbi.nlm.nih.gov/protein/NP_001186570.1.
Genbank® NCBI Accession No. NP_001300973, Version No. NP_001300973.1, “interleukin-33 isoform a precursor [*Homo sapiens*]”, available at https://www.ncbi.nlm.nih.gov/protein/NP_001300973.1.
Genbank® NCBI Accession No. NP_001300974, Version No. NP_001300974.1, “interleukin-33 isoform a precursor [*Homo sapiens*]”, available at https://www.ncbi.nlm.nih.gov/protein/NP_001300974.1.
Genbank® NCBI Accession No. NP_001300975, Version No. NP_001300975.1, “interleukin-33 isoform d [*Homo sapiens*]”, available at https://www.ncbi.nlm.nih.gov/protein/NP_001300975.1.
Genbank® NCBI Accession No. NR_029684, Version No. NR_029684.1, “*Homo sapiens* microRNA 143 (MIR143), microRNA”, available at https://www.ncbi.nlm.nih.gov/nuccore/NR_029684.1/.
Gilbert et al., “Production and characterization of ECM powder: implications for tissue engineering applications”, Biomaterials, 2005, pp. 1431-1435, vol. 26.
Gliwiński et al., “Cell-Based Therapies with T Regulatory Cells”, BioDrugs: Clinical Immunotherapeutics, Biopharmaceuticals and Gene Therapy, 2017, pp. 335-347, vol. 31:4.
Hamalainen et al., “Molecular cloning of human lysyl oxidase and assignment of the gene to chromosome 5q23. 3-31.2”, Genomics, 1991, pp. 508-516, vol. 11:508.
Hill et al., “Quantification of Extracellular Matrix Proteins from a Rat Lung Scaffold to Provide a Molecular Readout for Tissue Engineering*[S]”, Mol Cell. Proteomics, 2015, pp. 961-973, vol. 14:4.
Hoeppli et al., “Tailoring the homing capacity of human Tregs for directed migration to sites of Th1-inflammation or Intestinal regions”, Am J Transplant., 2019, pp. 62-76, vol. 19:1.
Huleihel et al., “Matrix-bound nanovesicles within ECM bioscaffolds”, Science Advances, 2016, vol. 2:6.
Huleihel et al., “Macrophage phenotype in response to ECM bioscaffolds”, Seminars in Immunology, 2017, pp. 2-13, vol. 29.
Huleihel et al., “Matrix bound nanovesicles recapitulate extracellular matrix effects on macrophage phenotype” Tissue Engineering Part A, 2017, pp. 1283-1294, vol. 23:21-22.
Hussey et al. “Matrix bound nanovesicle-associated IL-33 activates a pro-remodeling macrophage phenotype via a hon-canonical, ST2-independent pathway”, 2019, J Immunol Regen Med., 2019, vol. 3.
Hussey et al., “Lipidomics and RNA sequencing reveal a novel subpopulation of nanovesicle within extracellular matrix biomaterials”, Sci Adv., 2020, vol. 6:12.
Koyama et al., “A Clinical Trial with Adoptive Transfer of Ex Vivo-induced, Donor-specific Immune-regulatory Cells in Kidney Transplantation-A Second Report”, Transplantation, 2020, pp. 2415-2423, vol. 104:11.
Lamarche et al., “Guiding regulatory T cells to the allograft”, Curr Opin Organ Transplant., 2018, pp. 106-113, vol. 23:1.
Liu et al., “IL-33-mediated IL-13 secretion by ST2+ Tregs controls inflammation after lung injury”, JCI Insight, 2019, vol. 4:6.
Macdonald et al., “Alloantigen-specific regulatory T cells generated with a chimeric antigen receptor”, J Clin Invest., 2016, pp. 1413-1424, vol. 126:4.
miRBase Accession No. MI0000461, “Stem-loop sequence has-mir-145”, available at https://www.mirbase.org/cgi-bin/mirna_entry.pl?acc=MI0000461.
miRBase Accession No. MI0000269, “Stem-loop sequence has-mir-181a-2”, available at https://www.mirbase.org/cgi-bin/mirna_entry.pl?acc=MI0000269.
Nadig et al., “In vivo prevention of transplant arteriosclerosis by ex vivo-expanded human regulatory T cells”, Nat Med., 2010, pp. 809-813, vol. 16:7.
Neal et al., “The Basics of Artificial Antigen Presenting Cells in T Cell-Based Cancer Immunotherapies”, Journal of Immunology Research and Therapy, 2017, pp. 68-79, vol. 2:1.
Sanchez-Fueyo et al., “Applicability, safety, and biological activity of regulatory T cell therapy in liver transplantation”, Am J Transplant., 2020, pp. 1125-1136, vol. 20:4.
Sasaki et al., “Combined GM-CSF and G-CSF administration mobilizes CD4+CD25hiFoxp3hi Treg in leukapheresis products of rhesus monkeys”, Am J Transplant., 2020, pp. 1691-1702, vol. 20.

(56) References Cited

OTHER PUBLICATIONS

Trackman et al., "Cloning of rat aorta lysyl oxidase cDNA: complete codons and predicted amino acid sequence", Biochemistry, 1990, pp. 4863-4870 vol. 29.

* cited by examiner

G

H

MICROPARTICLE-ASSISTED Treg THERAPY FOR TREATMENT OF TISSUE INJURY AND FIBROSIS

CROSS REFERENCE TO RELATED APPLICATIONS

This application is the United States national phase of International Application No. PCT/US2021/028871, filed Apr. 23, 2021, and claims priority to U.S. Provisional Patent Application No. 63/015,038, filed Apr. 24, 2020, the disclosures of which are hereby incorporated by reference in their entirety.

STATEMENT REGARDING FEDERAL FUNDING

This invention was made with government support under Grant Nos. A1131453; HL122489; and AR073527 awarded by the National Institutes of Health. The government has certain rights in the invention.

Interleukin-33 (IL-33) is a unique and important reparative protein that is typically sequestered in the nucleus of stromal cells or natural microparticles embedded in the extracellular matrix (ECM). We have named these vesicles "Matrix Bound Vesicles (MBVs)" and shown that they are distinct from exosomes, contain immunoregulatory cargo, including IL-33, and effectively redirect hyperinflammation in several preclinical models. Our pre-clinical rodent studies and examination of clinical transplant samples establish that IL-33 is released after tissue injury to limit inflammatory immune responses and initiate tissue repair. Mice lacking IL-33 are highly susceptible to death after acute lung injury. In ongoing studies of skeletal injury, IL-33 deficient mice have significantly decreased function after muscle damage. We have also shown IL-33 is released during rejection of heart grafts and heart transplants from IL-33$^-$ deficient mice display dramatically augmented chronic rejection associated fibrosis and vessel disease. In all of these rodent models, the lack of IL-33 results in increased tissue pathology and augmented frequency and number of pro-inflammatory myeloid cells, including Ly6c$^+$ monocytes, Ly6c$^+$ iNOS$^+$ macrophages, and CD11c$^+$ MHCII$^{hi}$ monocyte-derived dendritic cells (mDC).

Despite these advances in understanding the role of IL-33 in inflammation and rejection, there is a need for improved treatments for inflammatory conditions and graft rejection.

SUMMARY

Recently, we have identified that a subset of regulatory T cells (Treg) express the IL-33 receptor ST2 and coordinate the generation of Arginase 1 (Arg1)$^+$ CD206$^{hi}$ macrophages with reparative functions in the response to released IL-33 through their secretion of IL-13. This response by Treg is independent of antigen-recognition by their TCR, but requires IL-33$^-$ mediated secretion of IL-13. Thus, we have identified a novel reparative function of Treg, targeting local macrophages, that is distinct from their better known and often therapeutically manipulated, TCR-dependent T cell suppressive activity. Our study of IL-33 deficient mice receiving muscle injury reveal that augmented lost function is associated with an almost complete absence of ST2$^+$ Treg early after insult. Delivery of IL-33$^+$ MBV improved muscle function and we establish the impact of delivered IL-33$^+$ vs IL-33$^-$ MBV on local Treg and macrophage populations.

The present disclosure relates to the concept, technology, and associated methods around Microparticle-Assisted Treg (MATr) therapy. MATr therapy is where Treg secreting reparative factors are generated in the laboratory and then supported at sites of injury or fibrosis through administered microparticles that sustain or augment their reparative responses. MATr therapy would have broad application potential as it can be initiated after tissue or organ injury due to infection, ischemia, surgery, pathogenic immune response, toxin exposure, or mechanical injury where it would serve to limit tissue damage and support constructive tissue remodeling to restore tissue or organ function.

Therefore, described herein is MATr therapy, which is the combination of Treg cell therapy and microparticle delivery of Treg-targeting stimuli, to address these several problems that persist in clinical medicine and lead to poor outcomes after tissue or organ injury. First, Treg, particularly ST2$^+$ IL-13$^+$ Treg cells are relatively rare cells in vivo. Second, extensive organ or tissue damage caused by surgery, major injuries, or sustained pro-inflammatory responses may overcome the reparative capacity of these limited endogenous Treg. Third, many injuries or injuries of certain tissue, such as cardiac or lung, often result in fibrosis and poor function. Thus, it is possible that large or sustained injuries deplete local IL-33 or other MBV cargo needed to sustain ST2$^+$ Treg-mediated repair.

To address, these problems we have developed both a) the methods to generate large numbers of IL-13$^+$ human Treg ex vivo and b) produce IL-33$^+$ MBV for clinical use.

A method of treating a patient having an injury or inflammatory condition is provided. The method comprises administering to the patient an amount of ex vivo-expanded regulatory T cells (Treg cells) effective to reduce inflammation in the patient, wherein the Treg cells are activated to produce IL-13$^+$ by IL 33$^+$ matrix-bound vesicles (IL-33$^+$ MBVs).

A method of implanting a graft in a patient is provided, comprising perfusing into the graft, or administering to the patient, an amount of ex vivo-expanded regulatory T cells (Treg cells) effective to reduce inflammation associated with implantation of the graft and/or rejection of the graft in the patient, wherein the ex vivo-expanded Treg cells are activated by IL 33$^+$ matrix-bound vesicles (IL-33$^+$ MBVs) prior to, during, or after perfusing the Treg cells into the graft or administering the Treg cells to the patient.

A method of implanting a graft in a patient is provided, comprising perfusing into the graft, or administering to the patient, an amount of ex vivo-expanded regulatory T cells (Treg cells) effective to reduce inflammation associated with implantation of the graft and/or rejection of the graft in the patient, wherein the ex vivo-expanded Treg cells are activated by IL 33$^+$ matrix-bound vesicles (IL-33$^+$ MBVs) prior to, during, or after perfusing the Treg cells into the graft or administering the Treg cells to the patient.

A method of producing activated ex vivo-expanded regulatory T cells (Treg cells) is provided, comprising expanding CD4$^+$CD25$^{hi}$Foxp3$^{hi}$ cells in vitro in culture medium comprising from $10^5$ to $10^{12}$ isolated IL-33$^+$ MBVs, producing an expanded population of CD4$^+$CD25$^{hi}$Foxp3$^{hi}$IL-13$^+$ Tregs, optionally in the presence of a natural or artificial antigen-presenting cell (APC).

A kit is provided, comprising one or more containers comprising from $10^5$ to $10^8$ ex vivo-expanded Treg cells, wherein the Treg cells are expanded in ex vivo in the presence of IL-33$^+$ MBVs to activate expression of IL-13 in the Treg cells, or the kit further comprises from $10^5$ to $10^{12}$ isolated IL-33$^+$ MBVs in a pharmaceutically-acceptable excipient.

Various aspects or embodiments of the present invention are described in the following numbered clauses.

Clause 1. A method of treating a patient having an injury or inflammatory condition, comprising administering to the patient an amount of ex vivo-expanded regulatory T cells (Treg cells) effective to reduce inflammation in the patient, wherein the Treg cells are activated to produce IL-13$^+$ by IL-33$^+$ matrix-bound vesicles (IL-33$^+$ MBVs).

Clause 2. The method of clause 1, wherein the Treg cells are activated by ex vivo co-culture with the IL-33$^+$ MBVs prior to administration to the patient.

Clause 3. The method of clause 1, wherein the Treg cells are activated by administration of IL-33$^+$ MBVs to the patient during or after administration of the Treg cells to the patient.

Clause 4. The method of any one of clauses 1-3, wherein the IL-33$^+$ MBVs are autologous, syngeneic, allogeneic, or xenogeneic to the patient.

Clause 5. The method of any one of clauses 1-3, wherein the Treg cells are autologous to the patient.

Clause 6. The method of any one of clauses 1-5, wherein the ex vivo-expanded Treg cells are expanded in culture medium comprising IL-33, and express and/or secrete IL-13, and optionally have the phenotype CD4$^+$CD25$^{hi}$Foxp3$^{hi}$IL-13$^+$.

Clause 7. The method of any one of clauses 1-6, wherein the Tregs are administered locally, to a site of injury or inflammation in the patient.

Clause 8. The method of any one of clauses 1-6, wherein the Tregs are administered parenterally to the patient.

Clause 9. The method of clause 8, wherein the Tregs are administered intravenously or intraperitoneally to the patient.

Clause 10. The method of any one of clauses 1-9, wherein the patient has a systemic inflammatory response syndrome (SIRS), such as cytokine release syndrome (CRS), and the Treg cells are administered parenterally, e.g., intravenously, to the patient.

Clause 11. The method of clause 10, wherein the patient has a respiratory viral infection, such as an influenza or a coronavirus infection, such as SARS-CoV2.

Clause 12. The method of any one of clauses 1-9, wherein the injury is ischemic or ischemia reperfusion injury, such as a myocardial infarct.

Clause 13. A method of implanting a graft in a patient, comprising perfusing into the graft, or administering to the patient, an amount of ex vivo-expanded regulatory T cells (Treg cells) effective to reduce inflammation associated with implantation of the graft and/or rejection of the graft in the patient, wherein the ex vivo-expanded Treg cells are activated by IL-33$^+$ matrix-bound vesicles (IL-33$^+$ MBVs) prior to, during, or after perfusing the Treg cells into the graft or administering the Treg cells to the patient.

Clause 14. The method of clauses 13, comprising: perfusing the graft with the ex vivo-expanded Treg and implanting the Treg-perfused graft in the patient.

Clause 15. The method of clause 13, comprising: implanting the graft and subsequently administering the ex vivo-expanded Treg cells to the patient.

Clause 16. The method of clause 15, wherein the IL-33+ MBVs are administered locally to the site of implantation of the graft.

Clause 17. The method of clause 15, wherein the IL-33+ MBVs are administered systemically to the patient.

Clause 18. The method of any one of clauses 13-17, wherein the Treg cells are activated by ex vivo co-culture with the IL-33$^+$ MBVs prior to perfusion into the graft or administration to the patient, and optionally wherein no IL-33$^+$ MBVs are administered to the patient.

Clause 19. The method of any one of clauses 13-17, wherein the Treg cells are activated by: perfusion of the IL-33$^+$ MBVs into the graft prior to, during, or after perfusion of the Treg cells into the graft, or administration of the IL-33$^+$ MBVs to the patient prior to, during, or after administration of the Treg cells to the patient.

Clause 20. The method of clause 13, comprising:

perfusing the graft with the IL-33$^+$ MBVs;

implanting the graft in the patient;

administering the ex vivo-expanded regulatory T cells (Treg cells) to the patient, wherein the IL-33$^+$ MBVs and Treg cells are administered in amounts and dosage regimens effective to reduce inflammation associated with implantation of the graft and/or rejection of the graft in the patient.

Clause 21. The method of any one of clauses 13-20, wherein the IL-33$^+$ MBVs are allogeneic or xenogeneic.

Clause 22. The method of any one of clauses 13-21, wherein the Treg cells are autologous to the patient.

Clause 23. The method of any one of clauses 13-22, wherein the ex vivo-expanded Treg cells are CD4$^+$CD25$^{hi}$Foxp3$^{hi}$IL-13$^+$, and optionally are expanded ex vivo in culture medium comprising IL-33.

Clause 24. The method of any one of clauses 1-23, further comprising, prior to administering the Treg cells to the patient, preparing the ex vivo-expanded Treg cells by expanding Treg cells in vitro in culture medium comprising IL-33, such as for from seven to 14 days, to produce ex vivo-expanded Treg cells that express and/or secrete IL-13, e.g., to produce CD4$^+$CD25$^{hi}$Foxp3$^{hi}$IL-13$^+$ Tregs.

Clause 25. The method of any one of clauses 1-24, wherein the ex vivo-expanded Treg cells are cryopreserved prior to perfusion into a graft or administration to the patient.

Clause 26. The method of any one of clauses 1-25, wherein from $10^5$ to $10^8$ of the ex vivo-expanded Treg cells are perfused into the graft or administered to the patient.

Clause 27. The method of any one of clauses 1-26, wherein from $10^5$ to $10^{12}$ IL-33$^+$ MBV particles are perfused into the graft or administered to the patient.

Clause 28. A method of producing activated ex vivo-expanded regulatory T cells (Treg cells), comprising expanding CD4+CD25hiFoxp3hi cells in vitro in culture medium comprising from 105 to 1012 isolated IL 33$^+$ MBVs, producing an expanded population of CD4+ CD25hiFoxp3hiIL-13+ Tregs, optionally in the presence of a natural or artificial antigen-presenting cell (APC).

Clause 29. A kit comprising a vessel comprising one or more containers comprising a container comprising from $10^5$ to $10^8$ ex vivo-expanded Treg cells, wherein the Treg cells are expanded in ex vivo in the presence of IL-33$^+$ MBVs to activate expression of IL-13 in the Treg cells, or the kit further comprises from 105 to $10^{12}$ isolated IL-33$^+$ MBVs in a pharmaceutically-acceptable excipient.

Clause 30. The kit of clause 29, wherein the ex vivo-expanded Treg cells are cryopreserved.

Clause 31. The kit of clause 29 or 30, wherein the ex vivo-expanded Treg cells are CD4$^+$CD25$^{hi}$Foxp3$^{hi}$IL-13$^+$ Tregs.

BRIEF DESCRIPTION OF THE DRAWINGS

(FIG. 4A) Cell numbers were counted throughout culture and the total cells per group for each donor at each timepoint presented. (FIGS. 4B and 4C) On culture day 25, expanded FoxP3+ tTeg were assessed by for flow cytometric analysis for intracellular IL-13. The data present are consistent and representative of multiple donors where we see increased when IL-33 is added to the aAPC/Treg cultures.

DETAILED DESCRIPTION

Figure 1:
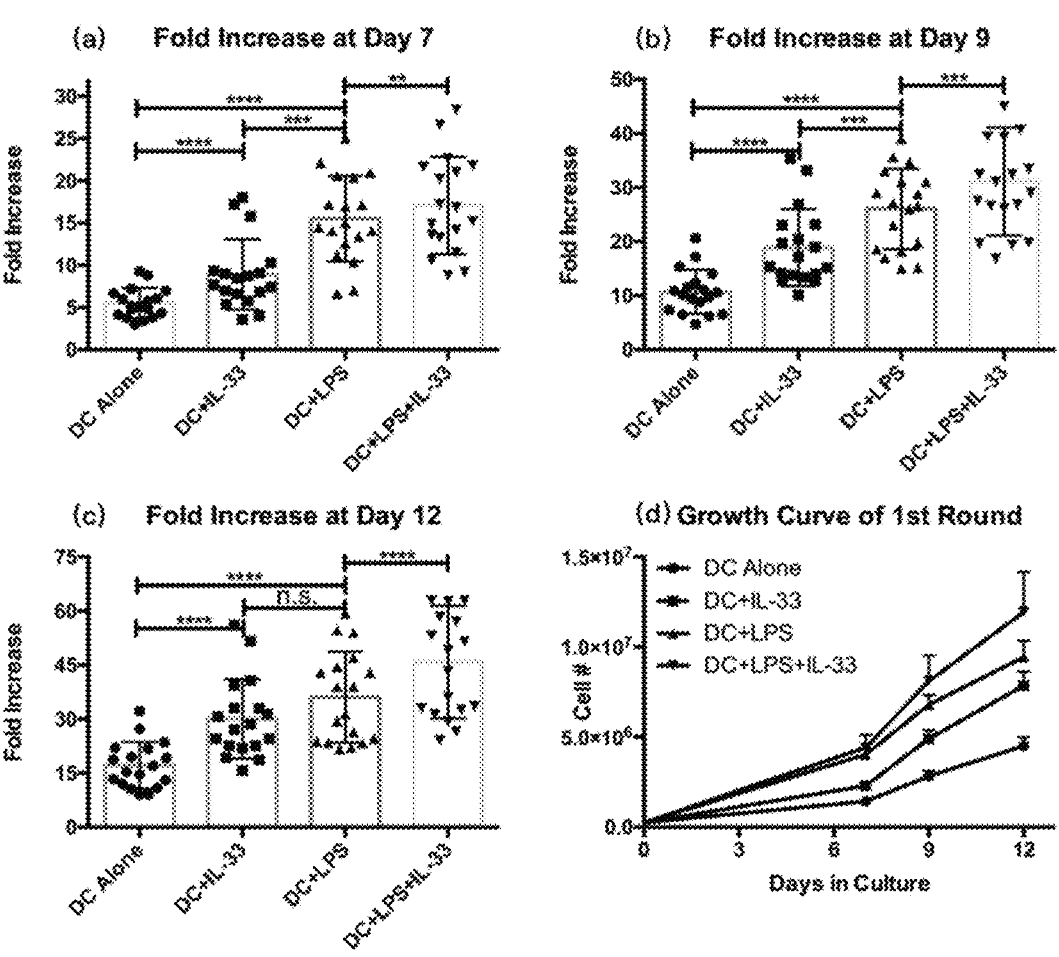
FIG. 1. Delivery of rIL-33 consistently increases the yield of human Treg in DC co-cultures (Condition A). Sorted Treg were stimulated using either immature DCs or LPS-stimulated mature DCs in the presence or absence of IL-33 in a ratio of 4:1 for 12 day using 300 U/ml of recombinant human IL-2 and recombinant human IL-33 (50 ng/ml). Cell numbers were counted throughout culture and the fold increase of cells was obtained using cell numbers divided by the starting number of Treg. The fold increase of expansion at day 7 (a), day 9 (b) and day 12 (c) and (d) the overall change in Treg numbers during the 12-day expansion period. Results represent 18 donor-recipient pairs from 9 independent experiments. Statistical significance was determined between each condition by paired, 2-tailed Student's t test. *P<0.05, P<0.01, *P<0.001, ****P<0.0001.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of a patient means administration to a patient by any suitable dosage regimen, procedure and/or administration route of a composition, device, or structure with the object of achieving a beneficial or desirable clinical/medical end-point, including but not limited to, preventing, reducing, and/or eliminating any symptom of inflammation, ischemia/reperfusion injury, graft rejection, autoimmune response, and mechanical or chemical tissue injury. An amount of any agent, administered by any suitable route, effective to treat a patient is an amount capable of preventing, reducing, and/or eliminating any symptom inflammation, ischemia/reperfusion injury, graft rejection, autoimmune response, and mechanical or chemical tissue injury in a patient. Any suitable clinical marker may be used to determine efficacy of treatment, including, without limitation, improved survival, reduced graft rejection, or improved repair or regeneration of tissue. Clinical assay results can be said to "normalize" when such clinical markers approach or enter a normal or healthy range for a patient.

Provided herein is an enhanced therapeutic method for use in the treatment of a patient in need of Treg therapy. Treg therapy may find use in a variety of diseases or conditions, such, as in regenerative medicine, transplantation, graft rejection, inflammatory disease or conditions, such as a "cytokine storm" arising from injury or infection. While in many patients, the inflammation process is controlled or controllable, and conditions that favor tissue repair and regeneration, such as, for example and without limitation, and without intent to be bound, by controlling local levels of G-CSF, IL-6, and MCP-1 and inhibiting accumulation of Ly6C$^{hi}$ monocytes, the activity of Treg cells can be overwhelmed locally or systemically. In such cases, Treg therapy may be indicated. The difficulty in Treg therapies is that sufficient Treg activity, even with administration of enriched populations of, e.g., autologous, syngeneic, or allogeneic exogenous Treg cells populations. As such, enhanced Treg therapies are needed. As described herein, the enhancement of therapies using IL-33 MBVs results in a superior anti-inflammatory, e.g., pro-regeneration/pro/repair, response.

Liu et al. (Liu, Q., Dwyer, G. K., Zhao, Y., Li, H., Mathews, L. R., Chakka, A. B., et al., (2019). IL-33-mediated IL-13 secretion by ST2$^+$ Tregs controls inflammation after lung injury. JCI Insight, 4(6). http://doi.org/10.1172/jci.insight.123919) identify a regulatory mechanism involving IL-33 after tissue injury that involves Treg secretion of IL-13 that is instrumental in limiting local inflammatory responses and able to shape the myeloid compartment after tissue injury. In this manuscript, we also establish that recombinant IL-33 can be used to generate IL-13$^+$ human Treg ex vivo.

An "isolated" biological component (such as a nucleic acid, protein, cell, or nanovesicle) has been substantially separated or purified away from other biological components in the cell of the organism or the ECM, in which the component naturally occurs.

The compositions described herein can be administered by any effective route, such as parenteral, e.g., intravenous, intramuscular, subcutaneous, intradermal, perfusion of organ or tissue, application to organ or tissue, etc., formulations of which are described below and in the below-referenced publications, as well as are broadly-known to those of ordinary skill in the art.

Suitable dosage forms may include single-dose, or multiple-dose vials or other containers, such as medical syringes, containing a composition comprising an active ingredient, such as a MBV as described herein.

Drug products, or pharmaceutical compositions comprising an active agent (e.g., drug), for example, an MBV and/or Treg cells as described herein, may be prepared by any method known in the art of pharmacy, for example, by bringing into association the active ingredient with the carrier(s) or excipient(s). As used herein, a "pharmaceutically acceptable excipient", "carrier", or "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable excipients include one or more of water, saline, phosphate buffered saline, dextrose, glycerol, ethanol, and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active agent. The active agent may be prepared with a carrier that will protect the compound against rapid release, such as a controlled release formulation, including implants, transdermal patches, and microencapsulated delivery systems. Biodegradable, biocompatible polymers can be used in delivery systems, such as ethylene vinyl acetate, polyanhydrides, polyglycolic acid, collagen, polyorthoesters, and polylactic acid. Methods for the preparation of such formulations are broadly-known to those skilled in the art.

Additionally, active agent-containing compositions may be in a variety of forms. The preferred form depends on the intended mode of administration and therapeutic application, which will in turn dictate the types of carriers/excipients. Suitable forms include, but are not limited to, liquid, semi-solid and solid dosage forms.

Pharmaceutical formulations adapted for oral administration may be presented, for example and without limitation, as discrete units such as capsules or tablets; powders or granules; solutions or suspensions in aqueous or non-aqueous liquids; edible foams or whips; or oil-in-water liquid emulsions or water-in-oil liquid emulsions. In certain embodiments, the active agent may be contained in a formulation such that it is suitable for oral administration, for example, by combining the active agent with an inert diluent or an assimilable edible carrier. The active agent (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical formulations adapted for topical administration may be formulated, for example and without limitation, as ointments, creams, suspensions, lotions, powders, solutions, pastes, gels, sprays, aerosols, or oils. Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents, and other suitable additives. Pharmaceutically acceptable organic or inorganic excipients suitable for non-parenteral administration which do not deleteriously react with nucleic acids can be used.

Pharmaceutical formulations adapted for nasal administration wherein the carrier is a solid include a coarse powder having a particle size, for example, in the range 20 to 500 microns which is administered in the manner in which snuff is taken, e.g., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include, without limitation, fine particle dusts or mists which may be generated by means of various types of metered dose pressurized aerosols, nebulizers, or insufflators. In the context of delivery of the active agents described herein by inhalation, inhalation drug products, such as metered-dose inhalers, as are broadly-known in the pharmaceutical arts, are used. Metered dose inhalers are configured to deliver a single dose of an active agent per actuation, though multiple actuations may be needed to effectively treat a given patient.

Pharmaceutical formulations adapted for parenteral administration include aqueous and non-aqueous sterile injection solutions which may contain, for example and without limitation, anti-oxidants, buffers, bacteriostats, lipids, liposomes, emulsifiers, also suspending agents and rheology modifiers. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets.

Other than living, cellular therapies, therapeutic compositions may be sterile and stable under the conditions of manufacture and storage. For example, sterile injectable solutions may be prepared by incorporating the active agent in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A "therapeutically effective amount" refers to an amount of a drug product or active agent effective, at dosages and for periods of time necessary, to achieve the desired therapeutic result. An "amount effective" for treatment of a condition is an amount of an active agent or dosage form, such as a single or multiple metered doses from a metered-dose inhaler, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. A therapeutically effective amount of an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A "prophylactically effective amount" refers to an amount effective, at dosages and for periods of time necessary, to achieve a desired prophylactic result. Typically, since a prophylactic dose is used in subjects prior to or at an earlier stage of disease, the prophylactically effective amount may be less than the therapeutically effective amount.

Dosage regimens may be adjusted to provide the optimum desired response (e.g., a therapeutic or prophylactic response). For example, a single bolus may be administered, several divided doses may be administered over time, or the composition may be administered continuously or in a pulsed fashion with doses or partial doses being administered at regular intervals, for example, every 10, 15, 20, 30, 45, 60, 90, or 120 minutes, every 2 through 12 hours daily, or every other day, etc. The dosage may be proportionally reduced or increased as indicated by the exigencies of the therapeutic situation. In some instances, it may be especially advantageous to formulate parenteral or inhaled compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In the context of the present disclosure, MBVs may be administered to a patient in any effective concentration as part of an MATr treatment regimen, for example in concentrations ranging from $10^6$ to $10^{12}$ particles per ml, with a total number of particles administered to the patient ranging from $10^6$ to $10^{12}$ particles. Treg cells may be administered in a perfusate, but more typically may be administered parenterally, for example intravenously, e.g., by intravenous infusion. Effective numbers of Treg cells may range from $10^4$ to $10^7$ cells/Kg or $10^5$ to $10^9$ per treatment. Effective amounts of Treg cells and MBV particles may be determined empirically, e.g., by monitoring relevant clinical markers, and administering additional Treg cells and/or MBVs to normalize any pertinent clinical marker value. Multiple doses of the MBVs and/or Treg cells may be administered, e.g., perfused or infused, at different times, for example in intervals of at least one hour, or longer, including daily, weekly, monthly, or yearly, and any interval therebetween, as needed. Physical delivery of the MBVs may include: intravenous infusion, injections at a site of injury, graft, or infection in the patient, or catheter perfusion of a tissue or organ of the patient, e.g., using occlusion and perfusion catheters.

In the context of transplantation of a graft, such as an organ or tissue, the graft may be perfused with a perfusate (perfusion solution) comprising a therapeutic agent. In organ transplantation, a perfusate may be used to preserve the organ. Perfusate often includes suitable salts, sugars, amino acids, buffers, rheology modifiers, and other ingredients, such as the iron chelators LK-614 and/or deferoxamine. MBVs may be added to the perfusate in any effective concentration as part of an MATr treatment regimen, for example in concentrations ranging from $10^6$ to $10^{12}$ particles per ml, with a total number of particles administered via perfusion ranging from $10^6$ to $10^{12}$ particles. Treg cells may also be administered in the perfusate, but more typically may be administered parenterally, e.g., intravenously, after transplant. Effective numbers of Treg cells may range from $10^5$ cell to $10^8$. Effective amounts of Treg cells and MBV particles may be determined empirically, e.g., by monitoring graft rejection and administering additional Treg cells and/or MBVs to normalize any pertinent clinical marker value. Multiple doses of the MBVs and/or Treg cells may be administered at different times, for example in intervals of at least one hour, or longer, including daily, weekly, monthly, or yearly, and any interval therebetween, as needed. Physical delivery of the MBVs may include injections at a site of injury, graft, or infection in the patient, or by catheter perfusion of a tissue or organ of the patient, e.g., using occlusion and perfusion catheters.

Interleukin (IL)-33: A member of the IL-1 superfamily of cytokines, a determination based in part on the molecules' β-trefoil structure, a conserved structure type described in other IL-1 cytokines, including IL-1a, IL-1β, IL-1Ra, and IL-18. In this structure, the 12 β-strands of the β-trefoil are arranged in three pseudorepeats of four β-strand units, of which the first and last b-strands are antiparallel staves in a six-stranded β-barrel, while the second and third pb-strands of each repeat form a β-hairpin sitting atop the β-barrel. IL-33 binds to a high-affinity receptor family member ST2. IL-33 induces helper T cells, mast cells, eosinophils and basophils to produce type 2 cytokines. Exemplary amino acid sequences for human IL-33 are provide in GENBANK® Accession Nos. NP 001186569.1, NP 001186570.1, NP 001300973.1, NP_001300974.1, and NP_001300975.1, all incorporated herein by reference. See, e.g., International Patent Publication No. WO 2005/079844 A2

Lysyl oxidase (Lox) is a copper-dependent enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. In vivo, this results in cross-linking of collagen and elastin, which plays a role in stabilization of collagen fibrils and for the integrity and elasticity of mature elastin. Complex cross-links are formed in collagen (pyridinolines derived from three lysine residues) and in elastin (desmosines derived from four lysine residues) that differ in structure. The genes encoding Lox enzymes have been cloned from a variety of organisms (Hamalainen et al., Genomics 11:508, 1991; Trackman et al., Biochemistry 29:4863, 1990; incorporated herein by reference). Residues 153-417 and residues 201-417 of the sequence of human lysyl oxidase have been shown to be important for catalytic function. There are four Lox-like isoforms, called LoxLl, LoxL2, LoxL3 and LoxL4.

Nanovesicles derived from ECM (also called matrix bound nanovesicles, MBVs) are disclosed in International Patent Publication No. WO 2017/151862 A1, which is incorporated herein by reference in its entirety. It is disclosed that nanovesicles are embedded in the extracellular matrix. These MBVs may be isolated and are biologically active. Matrix-bound vesicles (MBVs) containing IL-33 and uses for those MBVs are described in International Patent Publication No. WO 2019/213482 A1, which is incorporated herein by reference in its entirety to the extent it is consistent with the present disclosure (See, also, Hussey, G. S., Dziki, J. L., Lee, Y. C., Bartolacci, J. G., Behun, M., Turnquist, H. R., & Badylak, S. F. (2019). Journal of Immunology and Regenerative Medicine. Journal of Immunology and Regenerative Medicine, 3, 26-35. http://doi.org/10.1016/j.regen.2019.01.001, incorporated herein by reference for its technical disclosure).

A nanovesicle is an extracellular vesicle that is a nanoparticle of about 10 to about 1,000 nm in diameter. Nanovesicles are lipid membrane bound particles that carry biologically active signaling molecules (e.g., microRNAs, proteins) among other molecules. Generally, the nanovesicle is limited by a lipid bilayer, and the biological molecules are enclosed and/or can be embedded in the bilayer. Thus, a nanovesicle includes a lumen surrounded by plasma membrane. The different types of vesicles can be distinguished based on diameter, subcellular origin, density, shape, sedimentation rate, lipid composition, protein markers, nucleic acid content and origin, such as from the extracellular matrix or secreted. A nanovesicle can be identified by its origin, such as a matrix bound nanovesicle from an ECM, protein content and/or the miR content.

A "nanovesicle derived from an ECM", "matrix-bound nanovesicle", "MBV", or an "ECM-derived nanovesicle" all refer to the same matrix-bound particles, ranging in size from 10 nm to 1000 nm, present in the extracellular matrix, which contain biologically active signaling molecules such as protein, lipids, nucleic acid, growth factors, and cytokines that influence cell behavior. The terms are interchangeable, and refer to the same vesicles. These MBVs are embedded within, and bound to, the ECM and are not just attached to the surface. These MBVs are resistant harsh isolation conditions, such as freeze thawing and digestion with proteases such as pepsin, elastase, hyaluronidase, proteinase K, and collagenase, and digestion with detergents. Generally, these MBVs are enriched for miR-145 and optionally miR-181, miR-143, and miR-125, amongst others. These MBVs do not express CD63 or CD81, or express barely detectable levels of these markers ($CD63^{lo}CD81^{lo}$). The MBVs contain Iysl oxidase (Lox) on their surface. The ECM may be an ECM from a tissue, can be produced from cells in culture, or can be purchased from a commercial source. MBVs are distinct from exosomes. MBVs may be used for therapeutic purposes, either alone or with another ECM. MBVs may be used in biological scaffolds, either alone or with another ECM.

Extracellular matrices are disclosed, for example and without limitation, in U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety. However, an ECM can be produced from any tissue, or from any in vitro source wherein the ECM is produced by cultured cells and comprises one or more polymeric components (constituents) of native ECM. ECM preparations can be considered to be "decellularized" or "acellular", meaning the cells have been removed from the source tissue or culture.

The ECM may be isolated from a vertebrate animal, for example, from a mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. In specific non-limiting examples, the extracellular matrix is isolated from esophageal tissue, urinary bladder, small intestinal submucosa, dermis, umbilical cord, pericardium, cardiac tissue, or skeletal muscle. The ECM may comprise any portion or tissue obtained from an organ, including, for example and without limitation, submucosa, epithelial basement membrane, tunica propria, etc. The ECM may isolated from urinary bladder. ECM can be produced from tumor tissue.

The ECM may or may not include the basement membrane. The ECM may include at least a portion of the basement membrane. The ECM material may or may not retain some of the cellular elements that comprised the original tissue such as capillary endothelial cells or fibrocytes. The ECM may contain both a basement membrane surface and a non-basement membrane surface.

The ECM may be harvested from porcine urinary bladders (also known as urinary bladder matrix or UBM). Briefly, the ECM may be prepared by removing the urinary bladder tissue from a mammal, such as a pig, and trimming residual external connective tissues, including adipose tissue. All residual urine is removed by repeated washes with tap water. The tissue is delaminated by first soaking the tissue in a deepithelializing solution, for example and without limitation, hypertonic saline (e.g., 1.0 N saline), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. The relatively fragile epithelial basement membrane is invariably damaged and removed by any mechanical abrasion on the luminal surface. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze.

Automated robotic procedures involving cutting blades, lasers and other methods of tissue separation are also contemplated. After these tissues are removed, the resulting ECM consists mainly of epithelial basement membrane and subjacent tunica propria.

Figure 2:
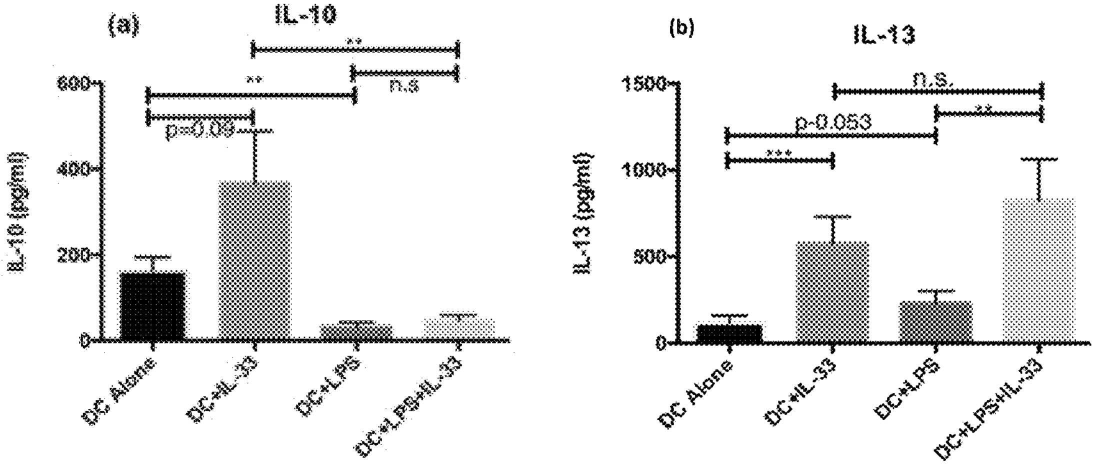
FIG. 2. The addition of IL-33 to DC culture augments Treg secretion of the important regulatory cytokines IL-13 and IL-10. The supernatant of cell culture media were harvested at day 12 at the end of expansion after centrifudge and the cytokine concentration was detected using a cytokine beads assay. Data shows the concentration of the cytokines in the supernatant of the culture media including (a) IL-10 and (b) IL-13. Data comes from samples representing 15 donor-recipient pairs from 7 independent experiments. Statistical significance was determined between each condition by paired, 2-tailed Student's t test. *P<0.05, P<0.01, *P<0.001.
Figure 3A:
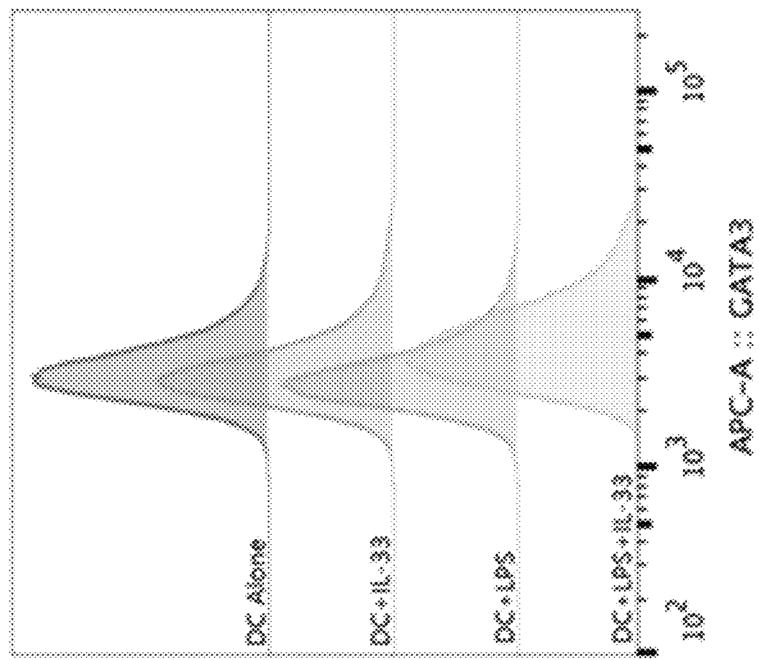
FIGS. 3A-3C. Culturing Treg with IL-33 increases expression of the IL-33 receptor ST2 and markers of Treg activation and differentiation after 7 days in culture with DC. Flow cytometric assessment of Foxp3$^+$ Treg revealed that culturing with IL-33 increased expression of the transcription factor GATA-3, which is important for Treg function, as well as the IL-33 receptor, ST2 which support Treg function. ICOS is a marker of activated and highly suppressive Treg. Results represent 18 donor-recipient pairs from 9 independent experiments. Statistical significance was determined between each condition by paired, 2-tailed Student's t test. *P<0.05, P<0.01, *P<0.001.
Figure 3A:
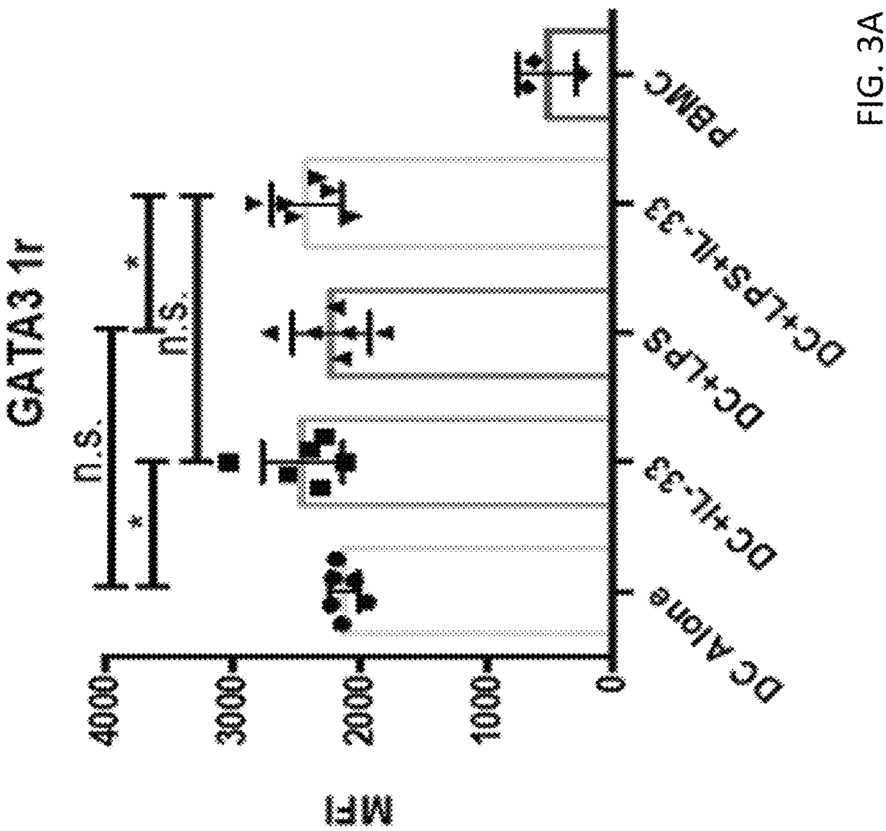
Figure 3B:
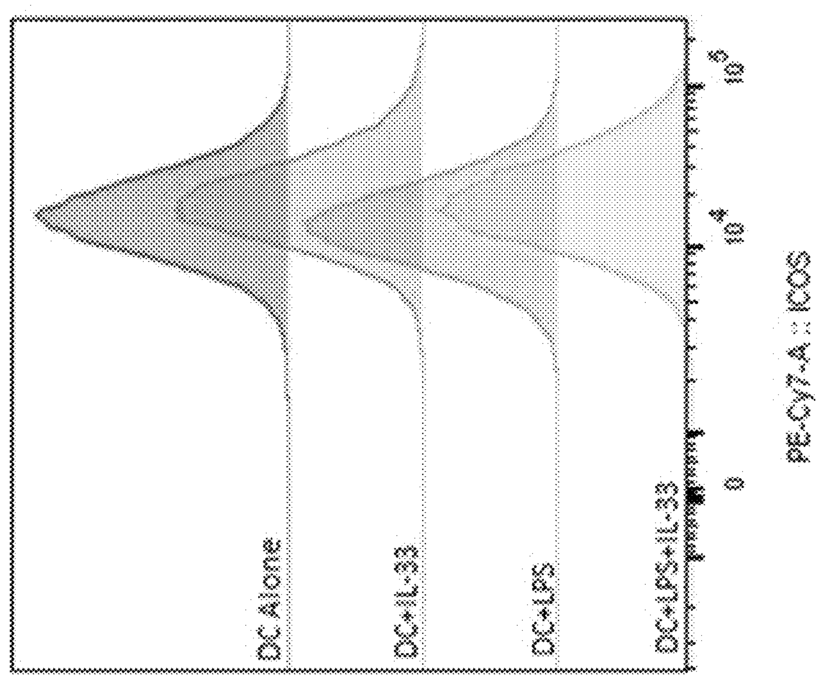
Figure 3B:
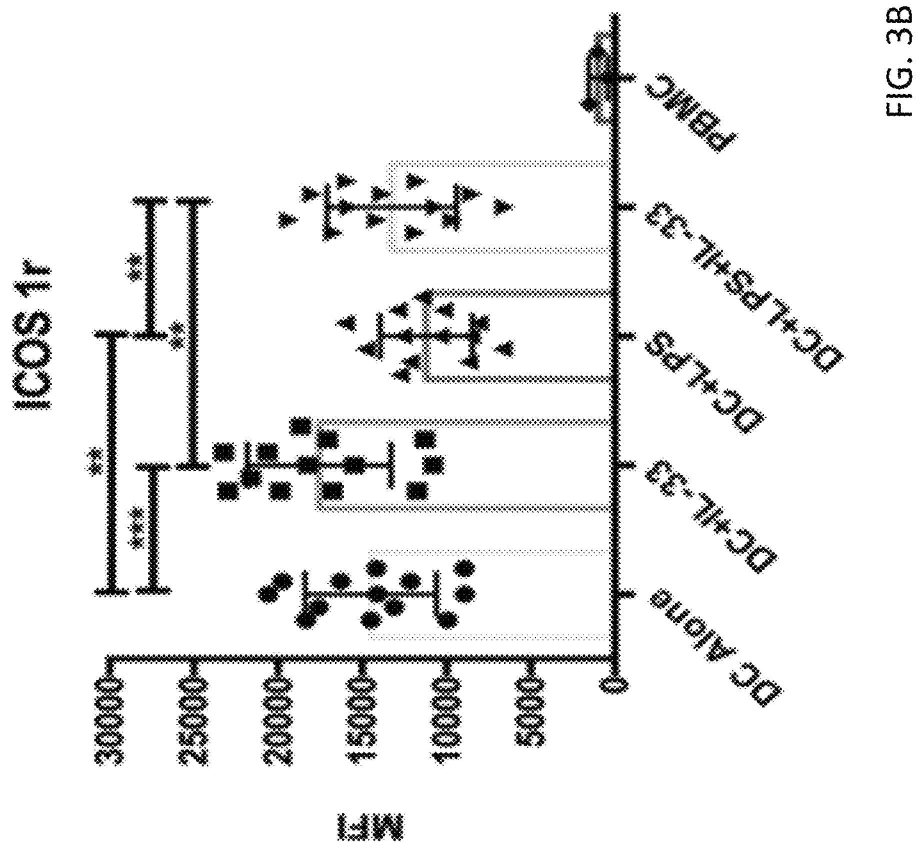
Figure 3C:
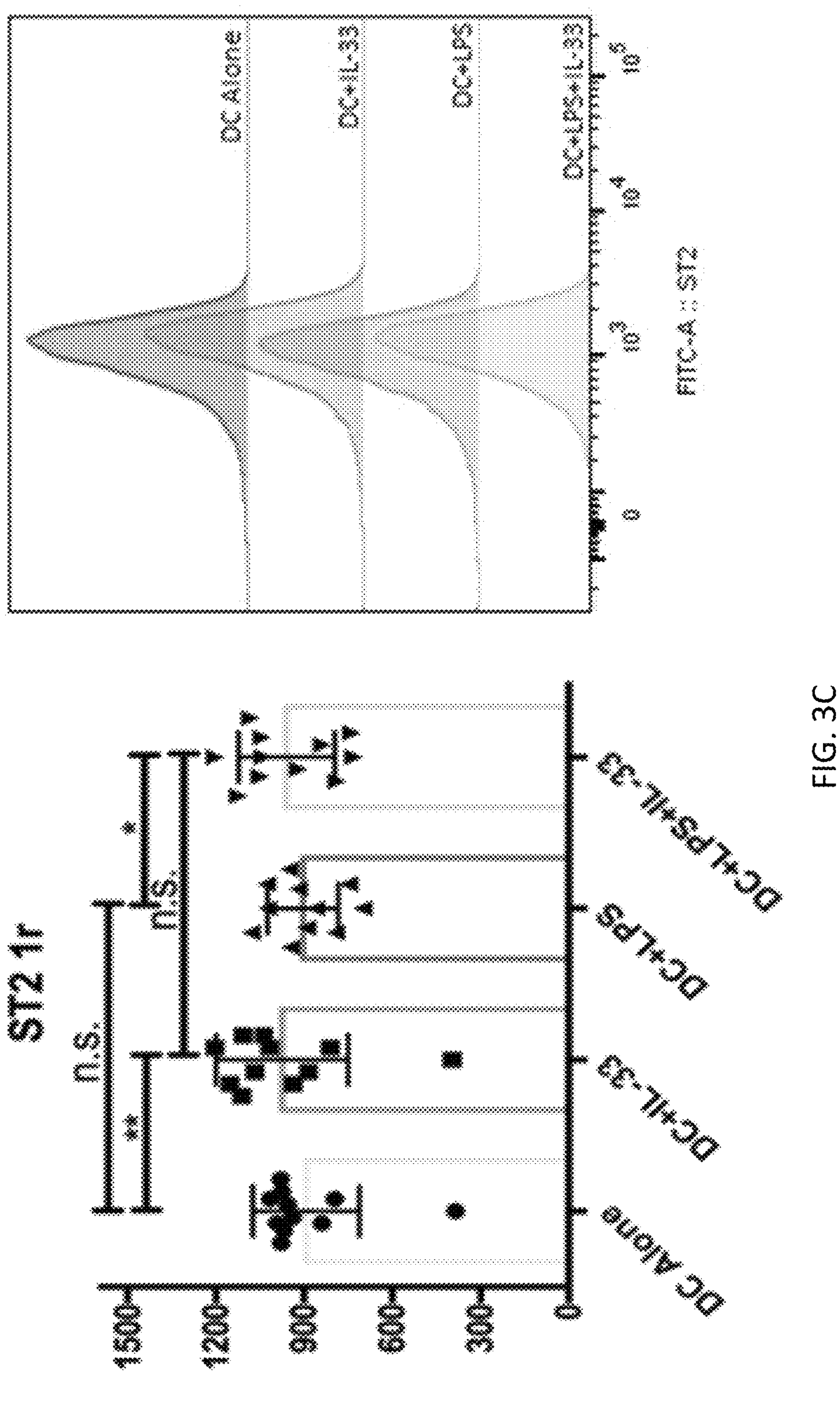
Figure 4A:
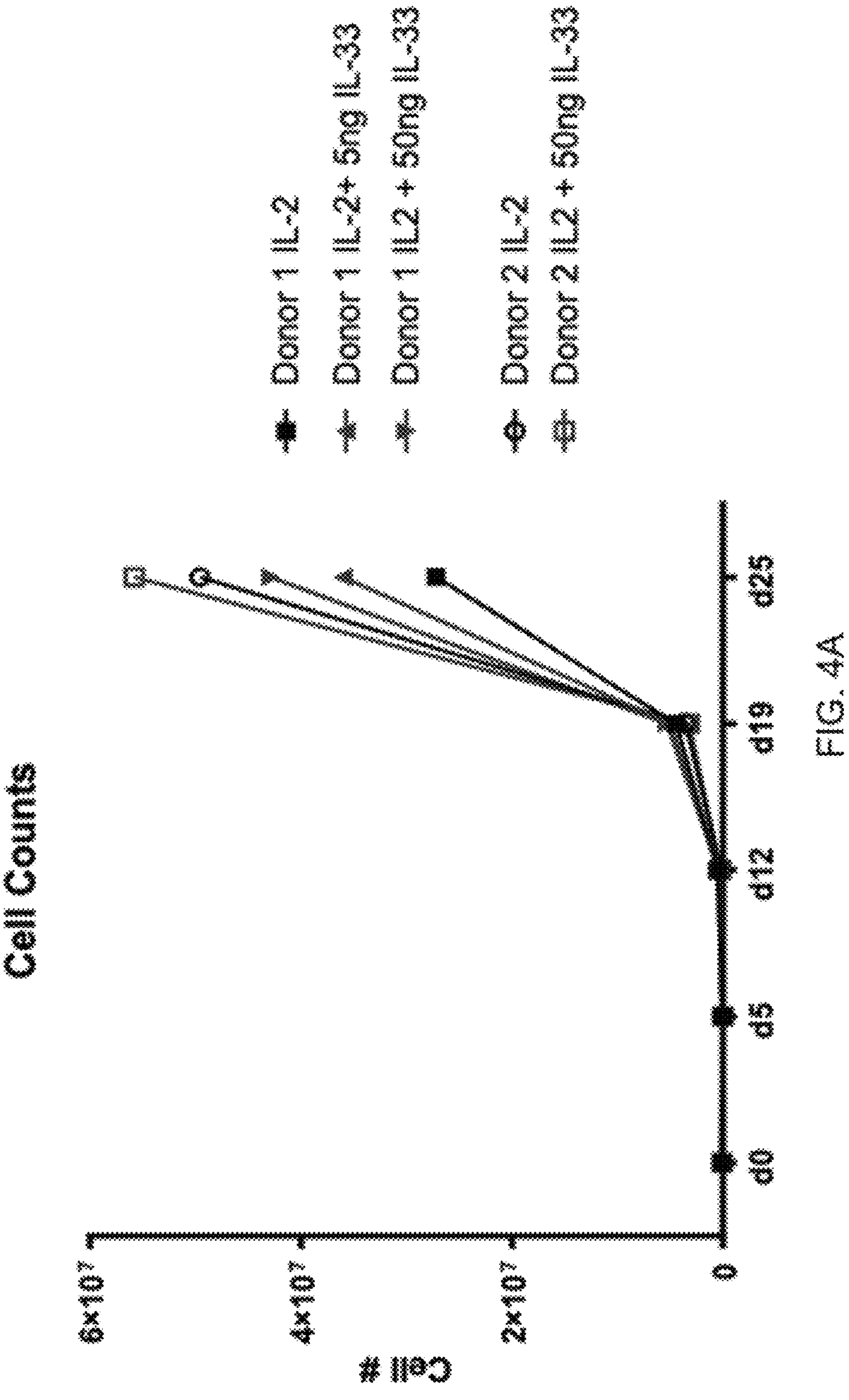
FIGS. 4A-4C. The addition of IL-33 consistently increases the yield of IL-13$^+$ human Treg in co-cultures with artificial APC (Condition B). Sorted Treg were stimulated with aAPC in the presence or absence of IL-33 in a ratio of 1:1 for 25 day using 500 U/ml of recombinant human IL-2 and recombinant human IL-33 (5 or 50 ng/ml).
Figure 4B:
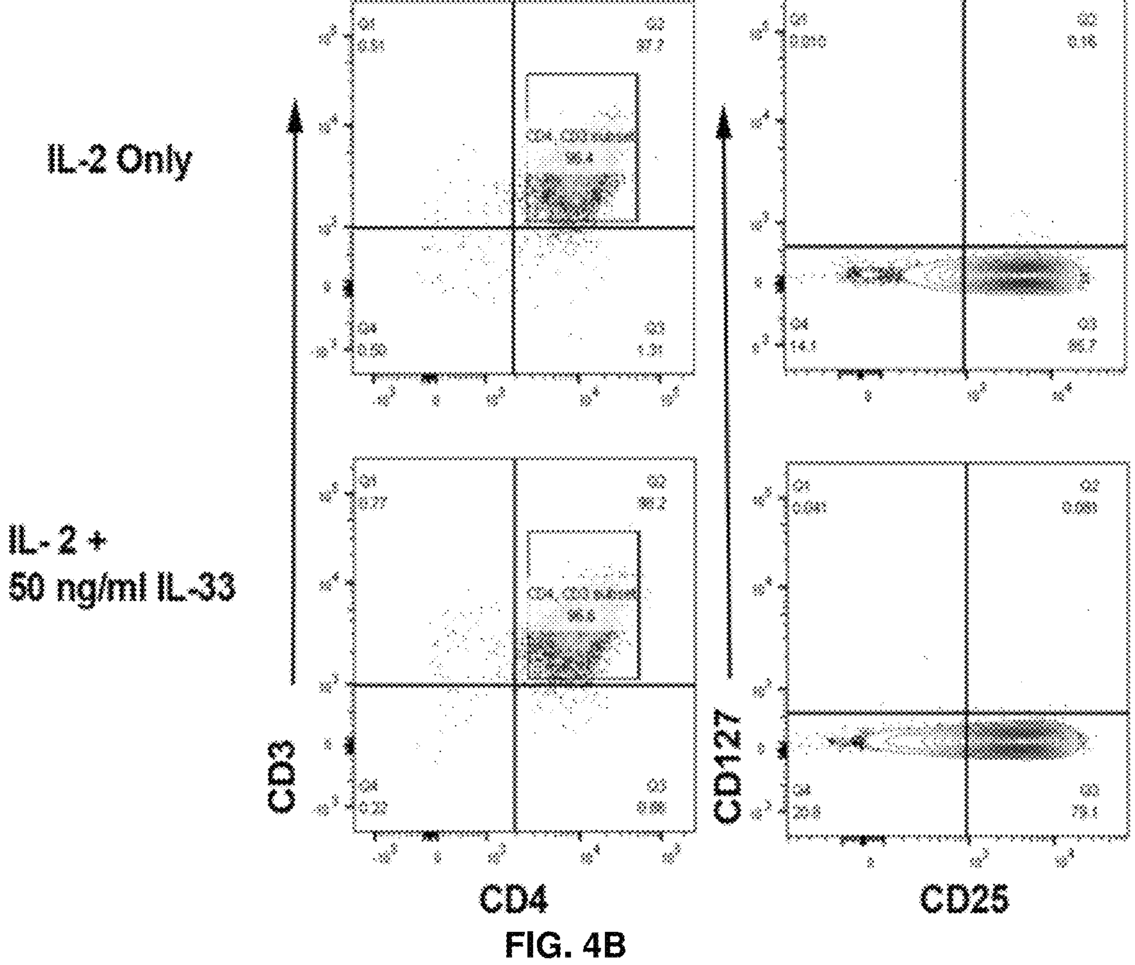
Figure 4C:
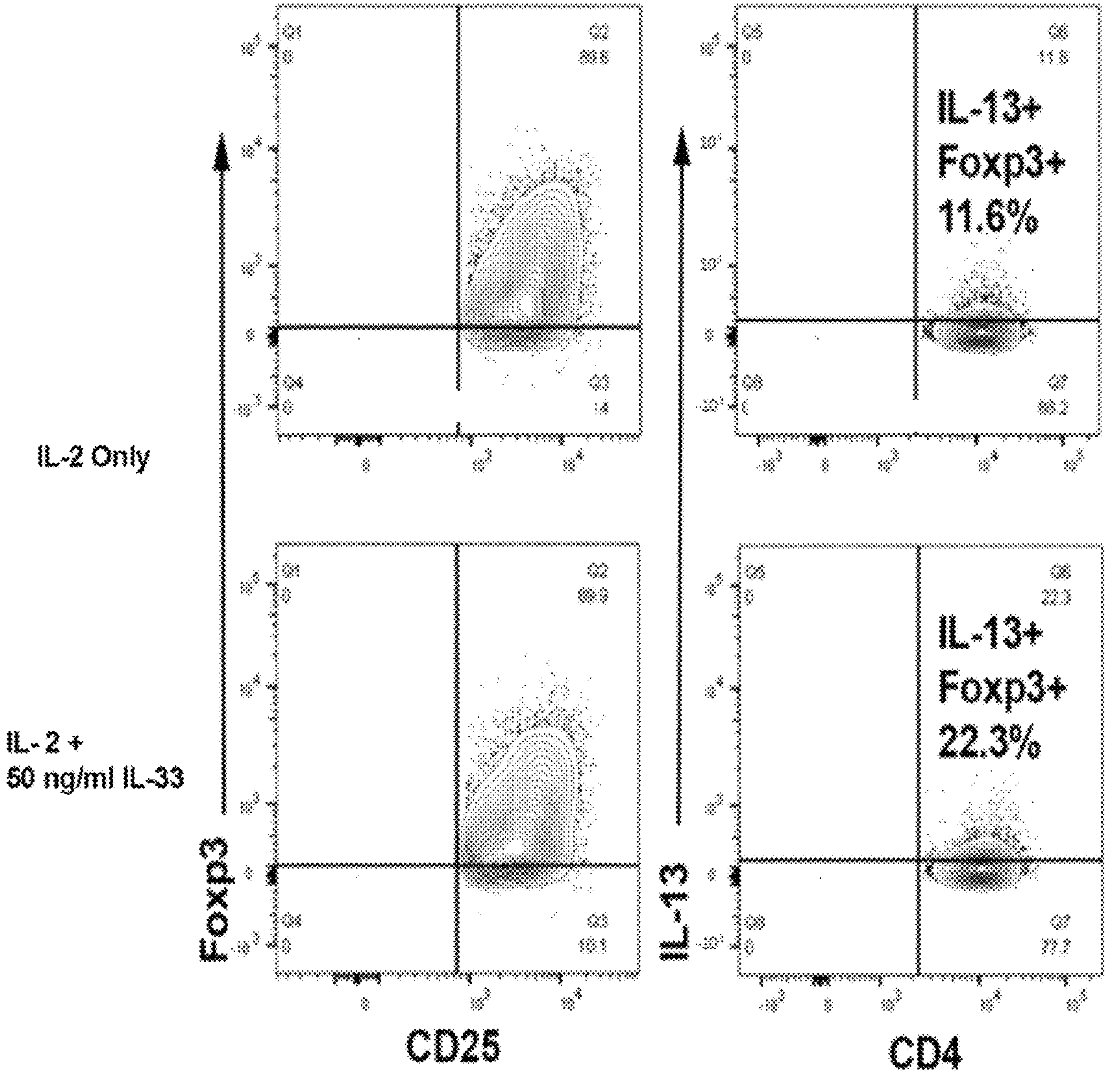

Alternatively, the ECM may prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa (see FIG. 2 of U.S. Pat. No. 9,277,999, which is incorporated herein by reference).

ECM may also be prepared as a powder. Such powder can be made according the method of Gilbert et al., Biomaterials 26 (2005) 1431-1435, herein incorporated by reference in its entirety. For example, UBM sheets can be lyophilized and then chopped into small sheets for immersion in liquid nitrogen. The snap frozen material can then be comminuted so that particles are small enough to be placed in a rotary knife mill, where the ECM is powdered. Similarly, by precipitating NaCl within the ECM tissue the material will fracture into uniformly sized particles, which may be snap frozen, lyophilized, and powdered.

In one non-limiting example, the ECM may be derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another non-limiting example, the ECM may be derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N J.).

In another embodiment, the ECM is derived from urinary bladder. Commercially available preparations include, but are not limited to UBM (ACell Corporation; Jessup, Md.).

MBVs may be derived from (obtained from or released from) an extracellular matrix using a method described below and/or in International Patent Publication Nos. WO 2017/151862 A1 and WO 2019/213482 A1. For example and without limitations, the ECM may be digested with an enzyme, such as pepsin, collagenase, elastase, hyaluronidase, or proteinase K, and the MBVs are isolated. In other embodiments, the MBVs are released and separated from the ECM by changing the pH with solutions such as glycine HCl, citric acid, ammonium hydroxide, use of chelating agents such as, but not limited to, EDTA, EGTA, by ionic strength and or chaotropic effects with the use of salts such as, but not limited to potassium chloride (KCl), sodium chloride, magnesium chloride, sodium iodide, sodium thiocyanate, or by exposing ECM to denaturing conditions like guanidine HCl or Urea.

In particular examples, the MBVs are prepared following digestion of an ECM with an enzyme, such as pepsin, elastase, hyaluronidase, proteinase K, salt solutions, or collagenase. The ECM may be freeze-thawed, or subject to mechanical degradation.

For IL-33$^{-}$ containing MBVs, the MBVs contain IL-33. In some examples, expression of CD63 and/or CD81 cannot be detected on the MBVs. Thus, the MBVs do not express CD63 and/or CD81. In another example, both CD63 and CD81 cannot be detected on the nanovesicles. In other examples, the MBVs have barely detectable levels of CD63 and CD81, such as that detectable by Western blot. These MBVs are CD63$^{lo}$CD81$^{lo}$. One of skill in the art can readily identify MBVs that are CD63$^{lo}$CD81$^{lo}$, using, for example, antibodies that specifically bind CD63 and CD81. A low level of these markers can be established using procedures such as fluorescent activated cell sorting (FACS) and fluorescently labeled antibodies to determine a threshold for low and high amounts of CD63 and CD81. The disclosed MBVs differ from nanovesicles, such as exosomes that may be transiently attached to the surface of the ECM due to their presence in biological fluids.

The MBVs include lysl oxidase (Lox). Generally, nanovesicles derived from the ECM have a higher Lox content than exosomes. Lox is expressed on the surface of MBVs. Nano-LC MS/MS proteomic analysis can be used to detect Lox proteins. Quantification of Lox may be performed as described (Hill, R C, et al., *Mol Cell Proteomics.* 2015; 14(4):961-73).

The MBVs may comprise one or more miRNA. In specific, non-limiting examples, the MBVs comprise one, two, or all three of miR-143, miR-145 and miR-181. MiR-143, miR-145 and miR-181 are known in the art.

An exemplary miR-145 nucleic acid sequence is provided in MiRbase Accession No. M10000461, incorporated herein by reference. An exemplary miR-145 nucleic acid sequence is: CACCUUGUCCUCACGGUCCAGUUUUCCCAG-GAAUCCCU UAGAUGCUAAGAUGGGGAUUCCUG-GAAAUACUGUUCUUGAGGUCAUGGUU (SEQ ID NO: 1). An exemplary miR-181 nucleic acid sequence is provided in miRbase Accession No. M10000269, incorporated herein by reference. An exemplary miR-181 nucleic acid sequence is: AGAAGGGCUAUCAGGCCAGCC-UUCAGAGGACUCCAAGGAACAUUCAACGCUG U CGGUGAGUUUGGGAUUUGAAAAAACCA-CUGACCGUUGACUGUACCUUGGGG UCCUUA (SEQ ID NO: 2). An exemplary miR-143 nucleic acid sequence is provided in NCBI Accession No. NR_029684.1, Mar. 30, 2018, incorporated herein by reference. An exemplary miR-143 nucleic acid sequence is: GCGCAGCGCC CUGU-CUCCCA GCCUGAGGUG CAGUGCUGCA UCUCUG-GUCA GUUGGGAGUC UGAGAUGAAG CACUGUAGCU CAGGAAGAGA GAAGUUGUUC UGCAGC (SEQ ID NO: 3).

Following administration, the MBVs may maintain expression of CD68 and CD-1 1b on macrophages in the subject. Nanovesicle treated macrophages may be predominantly F4/80+ Fizz1+, indicating an M2 phenotype. Thus, the macrophages may maintain an M2 phenotype.

The MBVs disclosed herein may be formulated into compositions for pharmaceutical delivery, and used in bioscaffolds and devices, for example as disclosed in International Patent Publication Nos. WO 2017/151862 A1 and WO 2019/213482 A1.

To produce MBVs, ECM may be produced by any cells or tissue of interest, or can be utilized from a commercial source, see above. The MBVs may be produced from the same species, or a different species, than the subject being treated. These methods may include digesting the ECM with an enzyme to produce digested ECM. More specifically, the ECM may be digested with one or more of pepsin, elastase, hyaluronidase, collagenase a metalloproteinase, and/or proteinase K. In a specific non-limiting example, the ECM is digested with only elastase and/or a metalloproteinase. In another non-limiting example, the ECM is not digested with collagenase and/or trypsin and/or proteinase K. In other examples, the ECM may be treated with a detergent. In examples, the method may not include the use of enzymes. In specific non-limiting examples, the method utilizes chaotropic agents or ionic strength to isolate MBVs such as salts, such as potassium chloride. The ECM may be manipulated to increase MBV content prior to isolation of MBVs.

In examples, the ECM is digested with an enzyme. The ECM may be digested with the enzyme for about 12 to about 48 hours, such as about 12 to about 36 hours. The ECM may be digested with the enzyme for about 12, about 24, about 36, or about 48 hours. In one specific, non-limiting example, the ECM is digested with the enzyme at room temperature. However, the digestion can occur at about 4° C., or any temperature between about 4° C. and 25° C. Generally, the ECM is digested with the enzyme for any length of time, and at any temperature, sufficient to remove collagen fibrils. The digestion process may be varied depending on the tissue source. Optionally, the ECM is processed by freezing and thawing, either before or after digestion with the enzyme. The ECM may be treated with detergents, including ionic and/or non-ionic detergents.

The digested ECM is then processed, such as by centrifugation, to isolate a fibril-free supernatant. In some embodiments the digested ECM is centrifuged, for example, for a first step at about 300 to about 1000 g. Thus, the digested ECM can be centrifuged at about 400 g to about 750 g, such as at about 400 g, about 450 g, about 500 g or about 600 g. This centrifugation can occur for about 10 to about 15 minutes, such as for about 10 to about 12 minutes, such as for about 10, about 11, about 12, about 13, about 14, or about 15 minutes. The supernatant including the digested ECM is collected.

The MBVs include Lox. Methods for isolating such MBVs may include digesting the extracellular matrix with elastase and/or metalloproteinase to produce digested extracellular matrix, centrifuging the digested extracellular matrix to remove collagen fibril remnants and thus to produce a fibril-free supernatant, centrifuging the fibril-free supernatant to isolate the solid materials, and suspending the solid materials in a carrier.

The digested ECM also may be centrifuged for a second step at about 2000 g to about 3000 g. Thus, the digested ECM may be centrifuged at about 2,500 g to about 3,000 g, such as at about 2,000 g, 2,500 g, 2,750 g or 3,000 g. This centrifugation may be performed for about 20 to about 30 minutes, such as for about 20 to about 25 minutes, such as for about 20, about 21, about 22, about 23, about 24, about 25, about 26, about 27, about 28, about 29, or about 30 minutes. The supernatant including the digested ECM is collected.

The digested ECM may be centrifuged for a third step at about 10,000 g to about 15,000 g. Thus, the digested ECM may be centrifuged at about 10,000 g to about 12,500 g, such as at about 10,000 g, 11,000 g, or 12,000 g. This centrifugation may be performed for about 25 to about 40 minutes, such as for about 25 to about 30 minutes, for example for about 25, about 26, about 27, about 28, about 29, about 30, about 31, about 32, about 33, about 34, about 35, about 36, about 37, about 38, about 39 or about 40 minutes. The supernatant including the digested ECM is collected.

One, two or all three of these centrifugation steps may be independently utilized. All three centrifugation steps may utilized. The centrifugation steps may be repeated, such as 2, 3, 4, or 5 times. In one example, all three centrifugation steps are repeated three times.

The digested ECM may be centrifuged at about 500 g for about 10 minutes, centrifuged at about 2,500 g for about 20 minutes, and/or centrifuged at about 10,000 g for about 30 minutes. These step(s), such as all three steps are repeated 2, 3, 4, or 5 times, such as three times. Thus, in one non-limiting example, the digested ECM is centrifuged at about 500 g for about 10 minutes, centrifuged at about 2,500 g for about 20 minutes, and centrifuged at about 10,000 g for about 30 minutes. These three steps may be repeated three times. Thus, a fibril-free supernatant is produced.

The fibril-free supernatant may then be centrifuged to isolate the MBVs. In some embodiments, the fibril-free supernatant is centrifuged at about 100,000 g to about 150,000 g. Thus, the fibril-free supernatant is centrifuged at about 100,000 g to about 125,000 g, such as at about 100,000 g, about 105,000 g, about 110,000 g, about 115,000 g, or about 120,000 g. This centrifugation may be performed for about 60 to about 90 minutes, such as about 70 to about 80 minutes, for example for about 60, about 65, about 70, about 75, about 80, about 85, or about 90 minutes. In one non-limiting example, the fiber-free supernatant is centrifuged at about 100,000 g for about 70 minutes. The solid material is collected, which is the MBVs. These MBVs then may be re-suspended in any carrier of interest, such as, but not limited to, a buffer.

In further examples the ECM is not digested with an enzyme. In these methods, ECM is suspended in an isotonic saline solution, such as phosphate buffered saline. Salt is then added to the suspension so that the final concentration of the salt is greater than about 0.1 M. The concentration may be, for example, up to about 3 M, for example, about 0.1 M salt to about 3 M, or about 0.1 M to about 2M. The salt may be, for example, about 0.1 M, 0.15 M, 0.2 M, 0.3 M, 0.4 M, 0.7 M, 0.6 M, 0.7 M, 0.8 M., 0.9 M, 1.0 M, 1.1 M, 1.2 M, 1.3 M, 1.4 M, 1.5 M, 1.6 M, 1.7 M, 1.8M, 1.9 M, or 2 M. In some non-limiting examples, the salt may potassium chloride, sodium chloride or magnesium chloride. In other embodiments, the salt may sodium chloride, magnesium chloride, sodium iodide, sodium thiocyanate, a sodium salt, a lithium salt, a cesium salt, or a calcium salt.

The ECM may be suspended in the salt solution for about 10 minutes to about 2 hours, such as about 15 minutes to about 1 hour, about 30 minutes to about 1 hour, or about 45 minutes to about 1 hour. The ECM may be suspended in the salt solution for about 15, 20, 25, 30, 35, 40, 45, 50, 55, 60, 65, 70, 75, 80, 85, 90, 95, 100, 105, 110, 115, or 120 minutes. The ECM may be suspended in the salt solution at temperatures from 4° C. to about 50° C., such as, but not limited to about 4° C. to about 25° C. or about 4° C. to about 37° C. In a specific non-limiting example, the ECM is suspended in the salt solution at about 4° C. In other specific non-limiting examples, the ECM is suspended in the salt solution at about 22° C. or about 25° C. (room temperature). In further non-limiting examples, the ECM is suspended in the salt solution at about 37° C.

The method may include incubating an extracellular matrix at a salt concentration of greater than about 0.4 M; centrifuging the digested extracellular matrix to remove collagen fibril remnants, and isolating the supernatant; centrifuging the supernatant to isolate the solid materials; and suspending the solid materials in a carrier, thereby isolating MBVs from the extracellular matrix.

Following incubation in the salt solution, the ECM may be centrifuged to remove collagen fibrils. The digested ECM may be centrifuged at about 2000 g to about 5000 g. Thus, the digested ECM may be centrifuged at about 2,500 g to about 4,500 g, such as at about 2,500 g, about 3,000 g, about 3,500 g, about 4,000 g, or about 4,500 g. In one specific non-limiting example, the centrifugation is at about 3,500 g. This centrifugation may be performed for about 20 to about 40 minutes, such as for about 25 to about 35 minutes, such as for about 20, about 21, about 22, about 23, about 24, about 25, about 26, about 27, about 28, about 29, about 30, about 31, about 32, about 33, about 34, or about 35 minutes. The supernatant is then collected.

The supernatant then may be centrifuged for a third step at about 100,000 to about 150,000 g. Thus, the digested ECM can be centrifuged at about 100,000 g to about 125,000 g, such as at about 100,000 g, 110,000 g or 120,000 g. This centrifugation may be performed for about 30 minutes to about 2.5 hour, such as for about 1 hour to about 3 hours, for example for about 30 minutes, about 45 minutes, about 60 minutes, about 90 minutes, or about 120 minutes (2 hours). The solid materials are collected and suspended in a solution, such as buffered saline, thereby isolating the MBVs.

The ECM is suspended in an isotonic buffered salt solution, such as, but not limited to, phosphate buffered saline. Centrifugation or other methods may be used to remove large particles. Ultrafiltration may then be utilized to isolate MBVs from the ECM, particles between about 10 nm and about 10,000 nm, such as between about 10 and about 1,000 nm, such as between about 10 nm and about 300 nm.

The isotonic buffered saline solution may have a total salt concentration of about 0.164 mM, and a pH of about 7.2 to about 7.4. The isotonic buffered saline solution may include 0.002 M KCl to about 0.164 M KCl, such as about 0.0027 M KCl (the concentration of KCl in phosphate buffered saline). This suspension may then be processed by ultracentrifugation.

Following incubation in the isotonic buffered salt solution, the ECM may be centrifuged to remove collagen fibrils. The digested ECM may be centrifuged at about 2000 g to about 5000 g. Thus, the digested ECM may be centrifuged at about 2,500 g to about 4,500 g, such as at about 2,500 g, about 3,000 g, about 3,500 g, about 4,000 g, or about 4,500 g. In one specific non-limiting example, the centrifugation is at about 3,500 g. This centrifugation may be performed for about 20 to about 40 minutes, such as for about 25 to about 35 minutes, such as for about 20, about 21, about 22, about 23, about 24, about 25, about 26, about 27, about 28, about 29, about 30, about 31, about 32, about 33, about 34, or about 35 minutes.

Microfiltration and centrifugation may be used and combined to remove large molecular weight materials from the suspension. In one example, large size molecule materials, such as more than 200 nm may be removed using microfiltration. In another embodiment, large size materials may be removed by the use of centrifugation. In a third embodiment both microfiltration and ultracentrifugation may be used to remove large molecular weight materials. Large molecular weight materials may be removed from the suspended ECM, such as materials greater than about 10,000 nm, greater than about 1,000 nm, greater than about 500 nm, or greater than about 300 nm.

The effluent for microfiltration or the supernatant may be then subjected to ultrafiltration. Thus, the effluent, which includes particle of less than about 10,000 nm, less than about 1,000 nm, less than about 500 nm, or less than about 300 nm may be collected and utilized. This effluent may then be subjected to ultrafiltration with a membrane with a molecular weight cutoff (MWCO) of 3,000 to 100,000, such as a 100,000 MWCO membrane.

Regulatory T cells (Tregs) are a population of lymphocytes whose role is to regulate and suppress excessive responses from other immune cells. Tregs may be CD4+ CD25+, and express Foxp3. Tregs are able to control a variety of other subsets, such as activated effector cells, e.g., T conventional (Tconv) cells, and inhibit antigen-presenting cells (APCs), natural killer (NK) cells, B cells, and innate immunity (See, e.g., Gliwiński, Mateusz et al., "Cell-Based Therapies with T Regulatory Cells." BioDrugs: clinical immunotherapeutics, biopharmaceuticals and gene therapy vol. 31,4 (2017): 335-347. doi:10.1007/s40259-017-0228-3, generally describing Treg cells, their function, and uses therefor, including ongoing trials).

United States Patent Publication No. US2015/0079026, incorporated herein by reference in its entirety, further described Treg cells, and exemplary methods of making and using cell populations thereof. Additional publications further describe the preparation and use of Treg cells, including, for example: U.S. Pat. No. 6,746,670; United States Patent Publication No 2009/0010950; Hoeppli R E, et al., *Am J Transplant.* 2019 January; 19(1):62-76 (Tailoring the homing capacity of human Tregs for directed migration to sites of Th1-inflammation or intestinal regions); Lamarche C, et al., Guiding regulatory T cells to the allograft. *Opin Organ Transplant.* 2018 February; 23(1):106-113; and MacDonald K G, et al., Alloantigen-specific regulatory T cells generated with a chimeric antigen receptor J Clin Invest. 2016 Apr. 1; 126(4):1413-24, each of which is incorporated herein by reference for its technical disclosure relating to isolating, making, and using Treg cell populations. The Tregs may be propagated in the presence of antigen-presenting cells (APC cells), including artificial APCs (aAPCs). Natural APCs include professional APCs such as dendritic cells, macrophages and B-cells, and may be xenogeneic, allogeneic, syngeneic, or autologous to the patient. aAPCs include engineered cells, or synthetic constructs comprising, for example and without limitation, antibodies, polymer beads, and/or stimulatory cytokines (see, e.g., Sasaki et al., Combined GM-CSF and G-CSF administration mobilizes CD4+ CD25$^{hi}$Foxp3$^{hi}$ Treg in leukapheresis products of rhesus monkeys. *Am J Transplant.* 2019 Dec. 27 and Neal, Lillian R, et al., "The Basics of Artificial Antigen Presenting Cells in T Cell-Based Cancer Immunotherapies." *Journal of Immunology Research and Therapy* (2017) 2(1):68-79).

Treg cell populations may be isolated, purified, obtained, and enriched by any method described herein or in the art, and include, for example and without limitation, use of cell sorting e.g., flow cytometry (e.g., fluorescence-activated cell sorting (FACS) or magnetic cell sorting). One non-limiting, and exemplary method described in US20090010950A1 includes the steps of:

a) purifying CD4$^+$ T cells from PBMCs;
b) separating CD25$^+$ from CD25$^-$ T cells;
c) cloning CD25$^+$ CD4$^+$ T cells by limiting dilution;
d) stimulating with phytohemagglutinin (PHA) or anti-CD3 mAb in the presence of IL-2; and
e) selecting the cell clones that display a constitutively high expression of CD25.

Further methods of preparing Treg cell populations are described below.

MBVs containing IL-33, and are of use to treat cardiac disease and disorders, and fibrotic diseases and disorders. In some non-limiting examples, the nanovesicles maintain expression of CD68 and CD-1 1b on macrophages in the subject.

Also provided herein is a method of expanding a Treg population ex vivo, comprising, co-culturing an enriched or purified population of Treg cells and an antigen-presenting cell (APC), such as a dendritic cell or an artificial APC (aAPC) (see, e.g., Sasaki et al. *Am J Transplant.* 2020 June; 20(6):1691-1702 and Neal, Lillian R, et al. *Journal of Immunology Research and Therapy* (2017) 2(1):68-79).

Prior to administration to a patient, the expanded Treg cells may be cultured ex vivo in the presence of MBVs containing IL-33 prior to administration to a patient. For example, within 40 hours, or 24 hours of administration to a patient, an amount of MBVs containing IL-33 effective to increase the therapeutic, anti-inflammatory, pro-regenerative activity of the Tregs is added to the culture producing MBV-activated Tregs. For example from $10^6$ to $10^{12}$ particles may be added to a culture vessel containing the Tregs.

Therapeutically, the MBV-activated Tregs may be administered to a patient, for example in amounts described above for treatment with co-administered MBVs. Effective numbers of MBV-activated Treg cells may range from $10^4$ to $10^7$ cells/kg or from $10^5$ to $10^9$ cells per treatment. The MBV-activated Tregs may be used locally or systemically, for treatment of a wound or injury, or for treatment of an inflammatory condition, such as systemically, or at a site of an infection, in a patient suffering from SIRS, e.g., CRS. The MBV-activated Tregs may be administered locally at a site of a graft or transplant or systemically in a transplant patient pre- and/or post-transplant, and/or the tissue to be grafted may be perfused or infused with the MBV-activated Tregs. The MBV-activated Tregs may be administered locally at a site of wound, graft, or fibrotic lesion to prevent or treat inflammation, fibrosis or scarring, or systemically, e.g., by parenteral or intravenous routes. In a patient with SIRS, e.g., CRS, the MBV-activated Tregs may be administered parenterally, e.g. locally at a site of infection, or systemically, for example intravenously. In a patient with pulmonary fibrosis or other inflammatory conditions of the lungs and/or respiratory tract, the MBV-activated Tregs may be administered locally, e.g., by spray, nebulization, aerosolization, inhalation, or by broncheoalveolar lavage, or systemically, for example intravenously.

Example 1—Isolation of Monocytes and Treg from Human PBMCs; Generation of Monocyte DC for Treg Expansion PBMCs are isolated from fresh human leukopacks (Central Blood Bank). Leukopacks are diluted with same amount of PBS at room temperature using 50 ml tube. 11 ml Ficoll-Paque Plus is slowly underlaid at the bottom of the 50 ml tube with diluted blood floating on the upper level. Samples are centrifuged at 1500 r/min for 25 minutes at room temperature. The PBMCs are located at the interface of the two layers after centrifugation. The PBMCs are collected and RBCs are lysed using ACK red blood cell lysis buffer. The cells are washed 1× with PBS and counted. Next, the PBMCs are incubated with human $CD14^+$ cells isolation kit reagents (Miltenyi Biotech, Auburn, CA) and for LS columns used for positive selection of $CD14^+$ cells with MACS magnetic. Isolated $CD14^+$ cells are cultured with RPMI 1640 media containing 5% human serum in a concentration of one million cell/ml. IL-4 and GM-CSF are both added at a concentration of 1000 U per ml. Cells are plated at 3 ml per well in a 6-well plate. At day 4, fresh media is added containing IL-4 and GM-CSF at the above concentration. Cells are harvested at day 7 using a brief incubation (5 minutes at 37° C.) in 2 mM EDTA in PBS to remove any adherent cells.

For Treg isolation, PBMC are isolated utilizing the same method as above. Treg are purified via a sequence of magnetic bead isolation steps beginning with the removal of CD8 and CD19 cells by positive selection using Miltenyi CD8 and CD19 microbeads and LS columns. The CD8/CD19 depleted cells are then enriched for CD4+ T cells using a CD4 purification kit and LD columns (Miltenyi) which applies an untouched method which positively selects CD4− cells. The resulting $CD4^+$ cells are then labeled with CD25 microbeads and isolated using Miltenyi MS columns. This final isolation yields CD4+ $CD25^+$ Treg and $CD4^+$ CD25− T cells, the Treg are then counted and a portion are conserved for Flow cytometric based phenotyping and the CD4+ CD25− cells are retained and cryopreserved to be used for downstream applications. The purity of the isolate Treg based on expression of Foxp3 is typically 95%.

Example 2—Method Using IL-33 in DC and Sorted Treg Cultures for the Expansion and Generation $IL\text{-}13^+$ Treg Collected DCs are washed and suspended in OpTmizer supplemented with 5% v/v human serum, 2 mM L-glutamine (Mediatech, Inc., Herndon, VA), 25 mM HEPES (Mediatech) and 55 μM β-2 mercaptoethanol (Invitrogen) and irradiate for 30Gy. DCs are plated in the 48 well plate at 50,000-100,000 cells per well in 0.25 ml OpTmizer. Sorted Tregs are plated at a ratio for 4 Treg to 1 DC. IL-2 and IL-33 are added in 0.5 ml OpTmizer at day 2 at a final concentration of 500-2000 U/ml for IL-2 and 20-200 ng/ml for IL-33. At day 4, replace half of the media with 0.5 ml OpTmizer containing same concentration of IL-33 and IL-2 as before. The color of OpTmizer is red, turning yellow indicating the total consumption of glucose and other nutrition. Depending on the growth of the culture, the next change is when the media indicators begin to turn to orange, typically around day 5 to day 7. At this time the concentration of cells is adjusted to a concentration of 1 million to 2 million cells to adequate volume and plate every 2 days. Cells around 2-3 million are placed in 12 well plate with 2-2.5 ml, cells more than 5 million are placed in 6 well plate with 3-4 ml. If larger number of cells occurred, cells can be placed in T25 flasks with 10 ml media or into a duplicate well in 6 well plate. Cells are counted at day 7. 9 and 12 and are harvested at day 12 for analysis and potential use as cell therapy. Verification of IL-13 production by Treg is completed using intracellular staining (Liu et al. *JCI Insight* 2019) or assessment of terminal culture supernatant cytokine levels using a Cytokine Bead Array. Suppressive function of expanded Treg is verified using a suppression assay.

Example 3—Method Using IL-33 in Artificial APC and Treg Cultures for Expansion and Generation IL-13+ Treg In this method, artificial antigen-presenting cells (aAPCs) (L-32) expressing CD32, CD80 and CD58 are used as described (Sasaki et al., "Combined GM-CSF and G-CSF administration mobilizes CD4+CD25hiFoxp3 hi Treg in leukapheresis products of rhesus monkeys", Am J Transplant. 2019 Dec. 27. doi: 10.1111/ajt.15761) with the modification of adding human IL-33 to generate IL-13+ Treg. For Treg expansion using artificial APC (L-32 cells), 5-7 days prior to Treg isolation, L-32 cells are plated and cultured until 90% confluency. 1 day prior to Treg isolation they are then harvested and irradiated at 8000 rads. The cells are seeded at a density of $1\times10^5$ in a 96 well U-bottom tissue culture plate. They are allowed to settle for about 2 hours and are then coated with anti-CD3 (0.2 ug/ml) (BD) and incubated overnight. Post isolation the Treg are then co-cultured at a ratio of 1:1 to the L-32 cells and are added to the U bottom plate. All wells receive 500 U/ml of huIL-2 (Peprotech) some wells receive 5 ng/ml to 100 ng/ml of recombinant huIL-33 (Biolegend). Media and cytokines are replenished every 2-3 days and every 5-6 days expanded Treg are restimulated with fresh L-32 cells. Treg products are verification for increased IL-13 production using intracellular staining or assessment of terminal culture supernatant cytokine levels using a Cytokine Bead Array. Suppressive function of expanded Treg is verified using a suppression assay.

Figure 5:
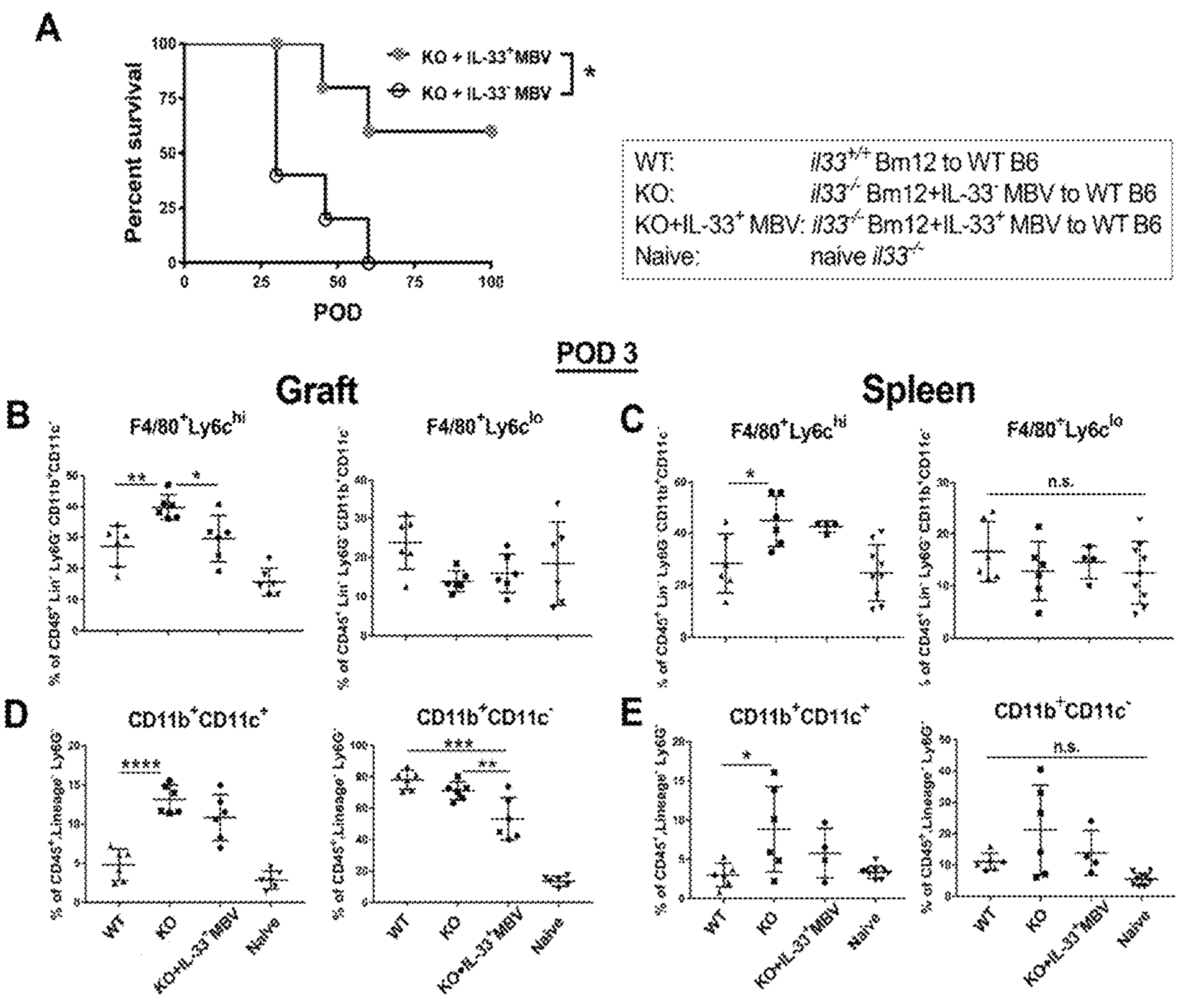
FIG. 5. Restoring local IL-33 reduces Ly6c$^{hi}$ inflammatory macrophages in the graft and limits chronic rejection of IL-33 deficient allografts. IL-33$^-$ deficient Bm12 (il33$^{-/-}$ Bm12) grafts were treated with matrix bound nanovesicles (MBV) generated from B6 il33$^{-/-}$ (IL-33$^-$ MBV) or il33$^{+/+}$ mice (IL-33$^+$ MBV) in hydrogel immediately after transplantation into B6 recipients (WT B6; n=6/group). (A) Graft survival of il33$^{-/-}$ Bm12 grafts treated with IL-33 containing MBV or IL-33-deficient MBV in WT B6 recipients. P values were calculated using a Kaplan-Meier analysis. *P<0.05. Graft infiltrating leukocytes (B, D) and splenocytes (C, E) at POD 3 from additional groups of WT B6 recipients of il33$^{-/-}$ Bm12 grafts treated with IL-33$^+$ MBV were compared to those receiving il33$^{+/+}$ Bm12 or il33$^{-/-}$ Bm12 grafts alone. Leukocytes from naïve Bm12 mice hearts and spleens were also included as baseline controls (Naïve; n=6). Quantification of F4/80$^+$ Ly6c$^{hi}$ and F4/80$^+$ Ly6c$^{lo}$ macrophages in the CD45.2$^+$ Lineage$^-$ Ly6G$^-$ CD11c$^-$ CD11 b$^+$ gated population (B, C) and CD11 b$^+$ CD11c$^+$ (DC), CD11b$^+$ CD11c$^+$ (monocytes) gated on CD45.2$^+$ Lineage$^-$ Ly6G$^-$ population (D, E) in the graft and spleen, respectively. P values were calculated using ANOVA. **P<0.001, *P<0.005, **P<0.01, *P<0.05.
Figure 6A:
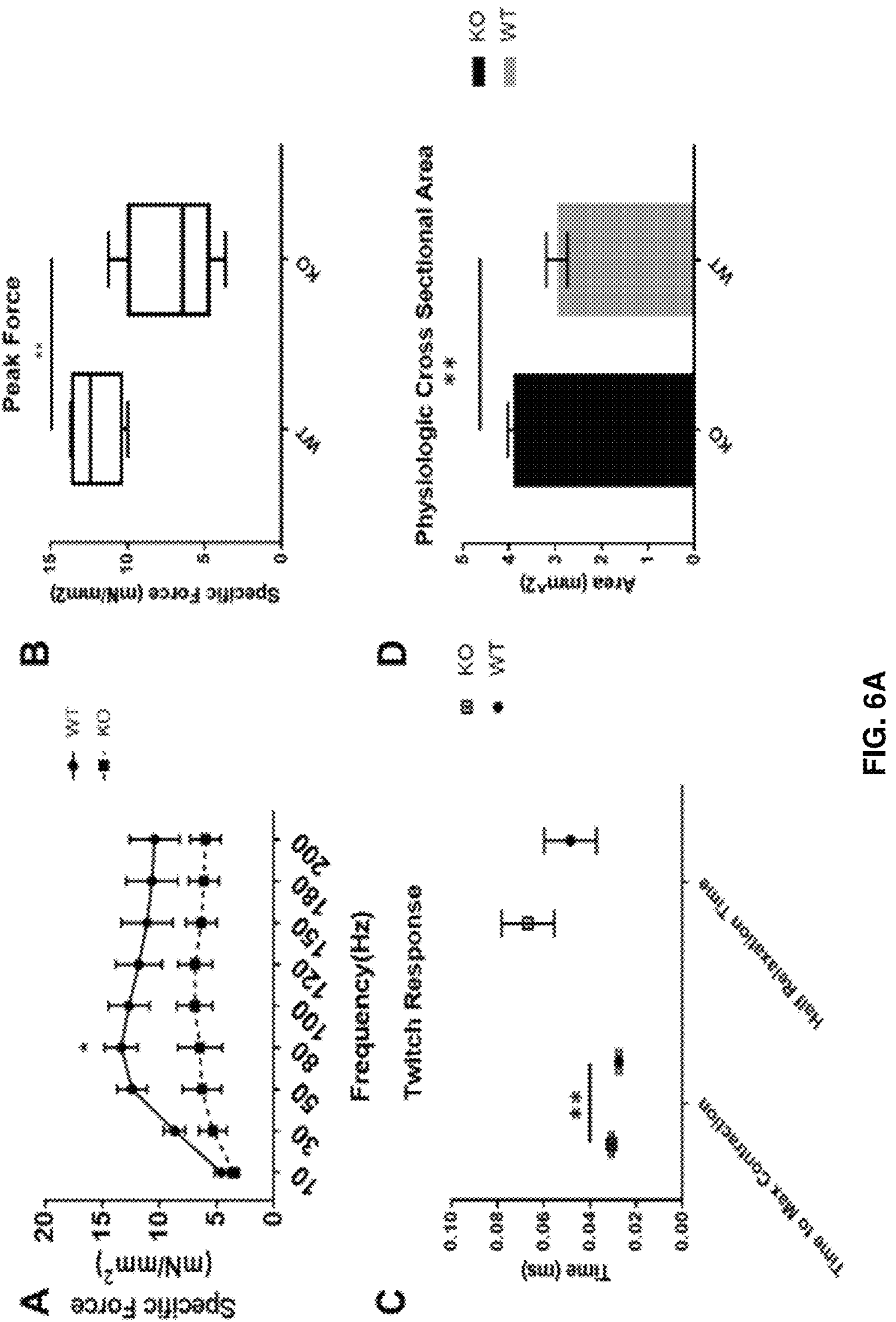
FIGS. 6A-6D. Increased inflammatory macrophages, decreased ST2+ Treg, and reduced functional recovery after skeletal tissue injury in the absence of IL-33. (A) In situ contractile testing of TA tetanic force generation as a function of frequency at POD-14 post-cardiotoxin injury shows significant reductions in functional output in mice lacking IL-33 at 80 Hz (p<0.05, n=6). (B) il33−/− mice shows significantly lower force output by POD-14 than wild-type counterparts (C-D) Twitch response of TA muscles at POD-14 after muscle injury shows that healed muscle of il33−/− mice had significantly different twitch characteristics and physiologic cross-sectional area compared to il33+/+ littermates (p<0.01, n=6). (E-H) Cardiotoxin muscle injury surgeries were performed on IL-33 expressing Arg-1$^{GFP}$ (WT B6) or IL-33 deficient Arg-1$^{GFP}$ B6 (KO B6). On POD3 and POD7, the injured muscles were harvested, and infiltrating leukocytes were assessed by flow cytometric analysis. (E-F) Representative dot plots and frequency for inflammatory macrophages in the CD45$^+$ CD3-B220-CD11 b$^+$Ly6G$^-$ gate. (G-H) Representative dot plots and frequency for ST2$^+$ Treg in the CD45$^+$CD3$^+$B220$^-$CD4$^+$ gate. (I-J) Quantification of immunolabeling for CD11b±Fizz1/iNOS shows significantly altered macrophage phenotype dynamics compared to wild-type animals. * p<0.05,  p<0.01, * p<0.001.
Figure 6B:
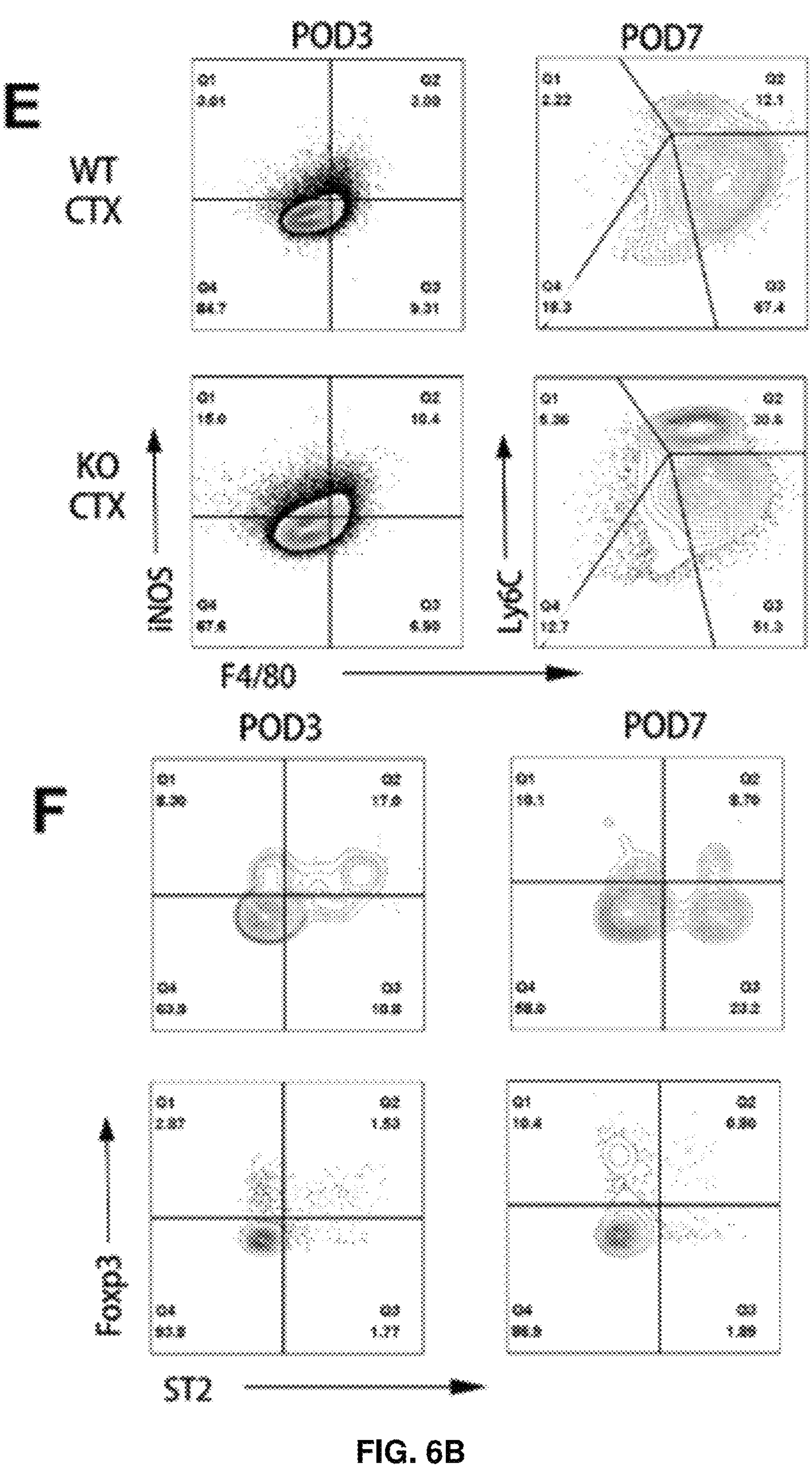
Figure 6C:
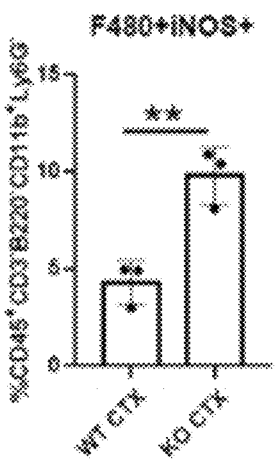
Figure 6C:
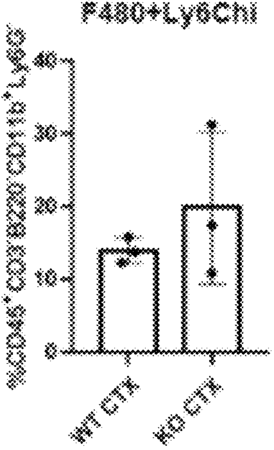
Figure 6C:
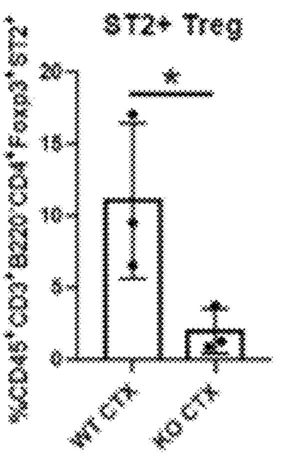
Figure 6C:
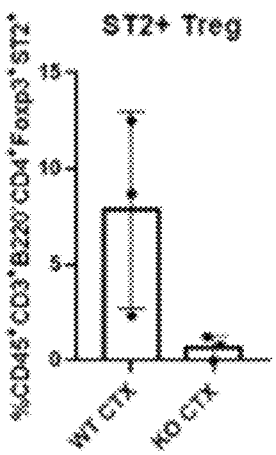
Figure 6D:
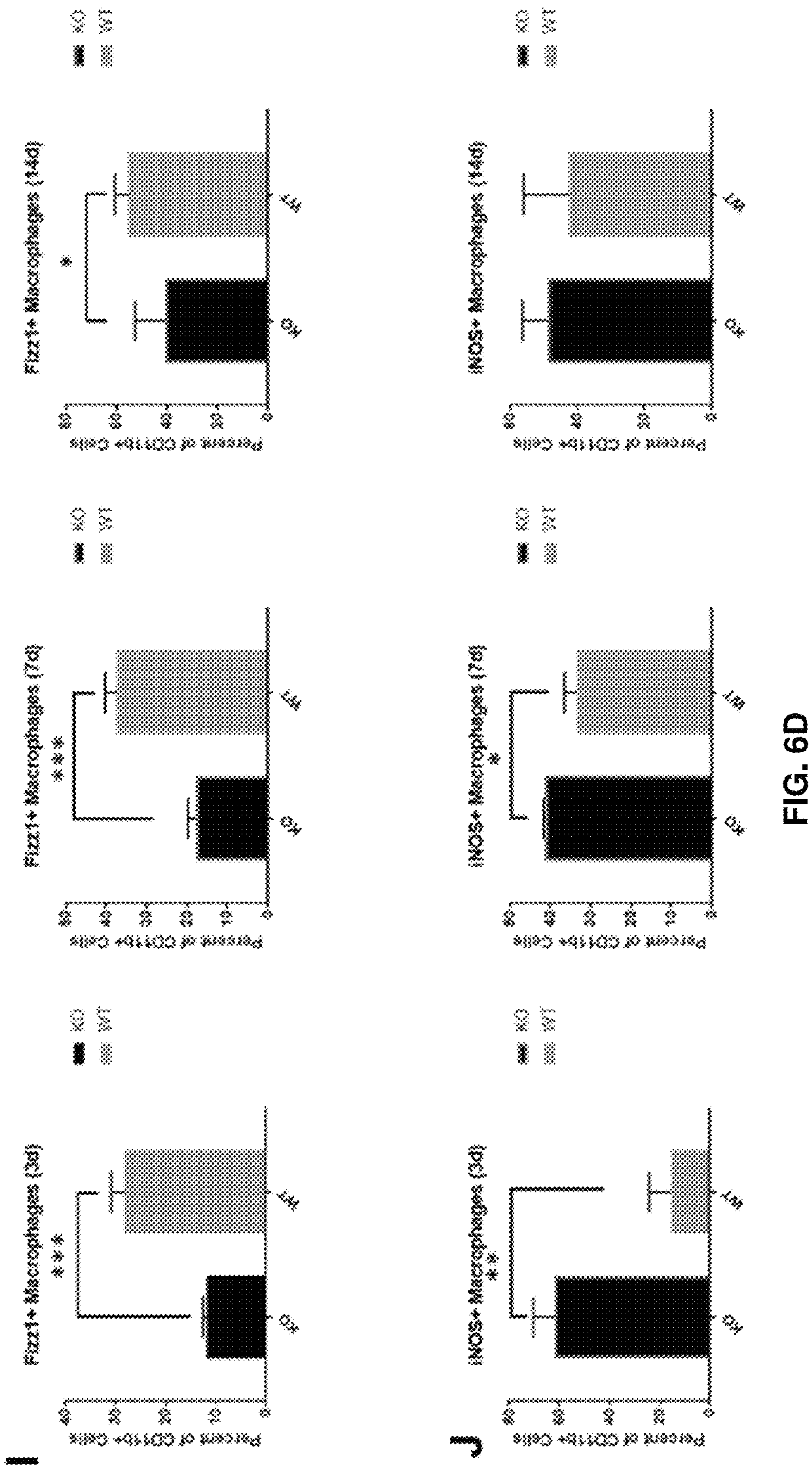
Figure 7:
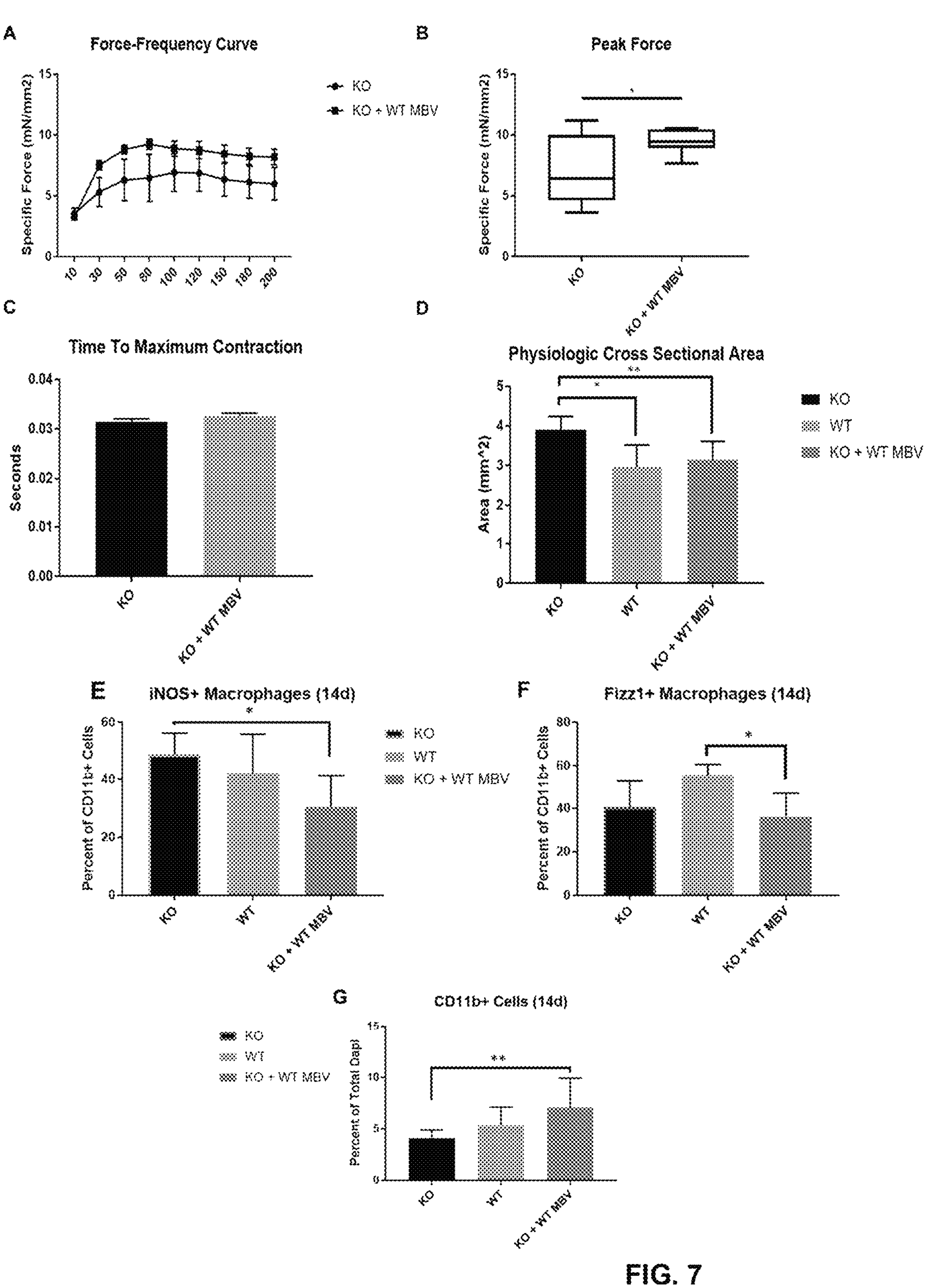
FIG. 7. Restoration of IL-33 using IL-33$^+$ MBV after skeletal injury improves function, reduces inflammatory macrophages and increases total macrophage presence. (A-B) In situ contractile testing of TA tetanic force generation at POD-14 post-cardiotoxin injury shows improved peak force production following exogenous provision of IL-33+ MBV compared to untreated counterparts (p≤0.05, n=5 (untreated il33−/−) and n=6 (IL-33$^+$ MBV-treated animals, one-tailed t-test) (C-D) Twitch response of TA muscles at POD-14 after muscle injury shows that healed muscle of untreated il33−/− mice and il33−/− mice treated with IL-33$^+$ MBV had significantly different half relaxation times and physiologic cross-sectional areas (p<0.0001 and p<0.01, respectively, one-tail t-test). (E-G) Immunolabeling of IL-33$^+$ MBV-treated il33−/− mouse skeletal muscle at POD-14 post-cardiotoxin skeletal muscle injury. (E) Quantification of immunolabeling against CD11b+iNOS+ M1-like macrophage population shows significant reductions in total iNOS+ macrophages as a result of MBV administration (N=6, one-way ANOVA). (F) Quantification of immunolabeling against CD11b+Fizz1+ M2-like macrophage population shows MBV do not increase total Fizz1$^+$ cells (N=6, one-way ANOVA). (C) Total CD11b+ macrophages were significantly elevated following MBV administration (N=6, one-way ANOVA). ** p<0.0001, * p<0.001, ** p<0.01, *p<0.05.
Figure 13:
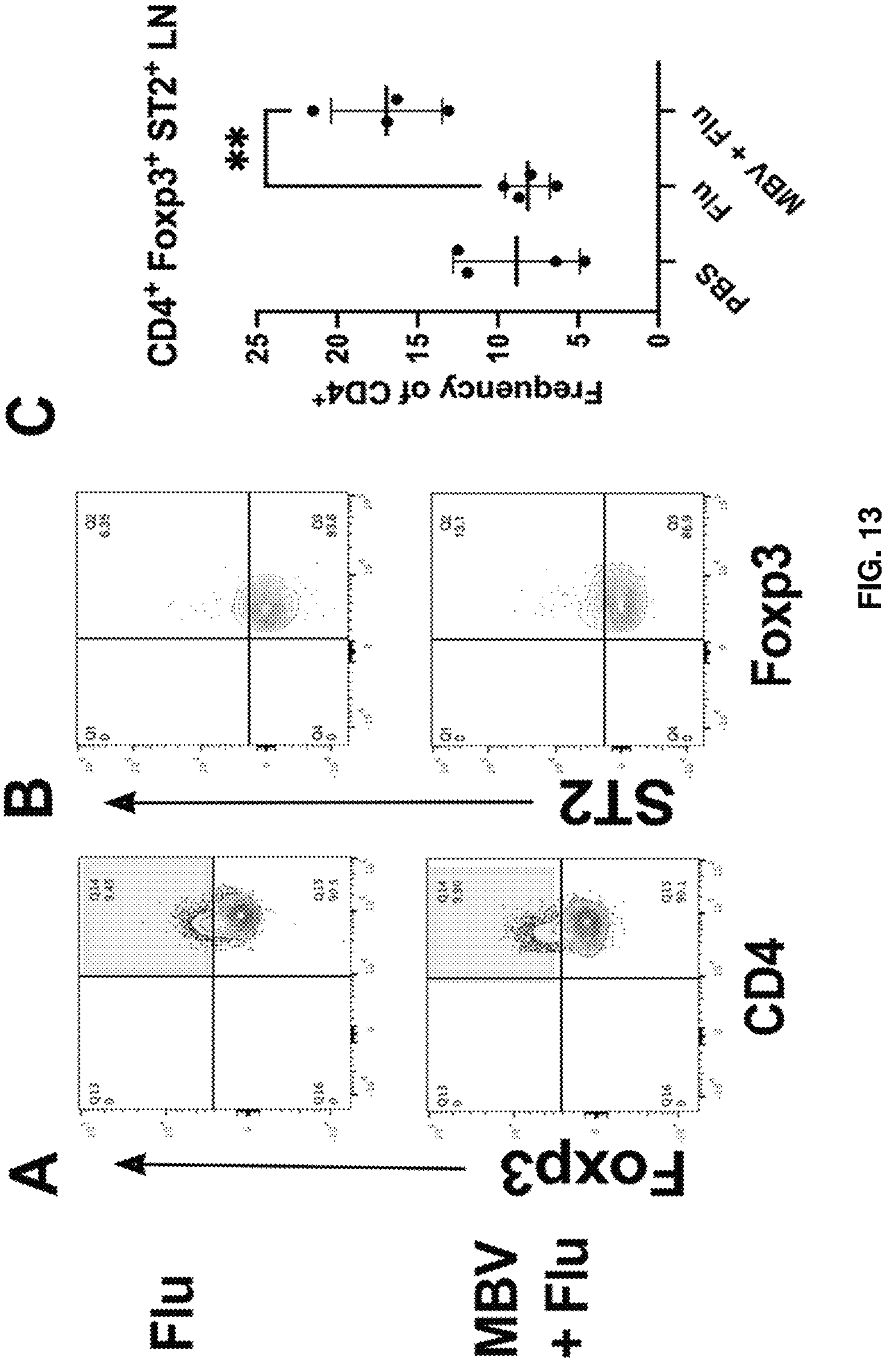
FIG. 13 shows that the delivery of MBV can expand presumed reparative CD4$^+$ ST2$^+$ Treg. In these data, systemic administration of MBV via intravenous delivery substantially increased the frequency of reparative CD4$^+$ ST2$^+$ Foxp3$^+$ in the lymph node during a pro-inflammatory lung infection. To complete these studies intra-tracheal inoculation with H1 N1 influenza on day 0 was followed by intravenous administration of MBV at day 2 and day 6. Representative flow cytometric data show how our assessment of CD45$^+$ CD4$^+$ Foxp3$^+$ lymphocytes (A) on day 7 provide proof-of-principle evidence for the ability of MBV delivery to significantly increase the frequency of ST2$^+$ subset of CD4$^+$ Foxp3$^+$ Treg (B) and (C).

FIGS. 1-4C provide data supporting the capacity of IL-33 added to human Treg cultures to increase the expansion of $IL\text{-}13^+$ $Foxp3^+$ Treg in both expansion conditions A (DC) and B (Artificial APC). FIGS. 5-7 provide data establishing the functional importance of $IL\text{-}33^+$ MBV for local differentiation reparative macrophages and $ST2^+$ Treg presence. See, also, FIG. 13, relating to inflammation produced by influenza infection and the capacity of MBVs to expand Tregs under such inflammatory conditions.

Example 4—Method Using $IL\text{-}33^+$ MBV in Treg Cultures for Expansion and Generation $IL\text{-}13^+$ Treg Expanded populations of $IL\text{-}13^+$ Treg cells are prepared essentially as described in Examples 2 and 3, substituting $IL\text{-}33^+$ MBVs for recombinant IL-33. From $10^5$ to $10^{12}$ $IL\text{-}33^+$ MBV particles isolated from allogeneic, syngeneic, or xenogenic tissues are used to produce activated Treg cells ($IL\text{-}13^+$ Treg cells). From $10^5$ to $10^9$ Treg cells are administered to a patient at a site of inflammation, injury, or graft, or systemically to treat inflammation in the patient to reduce inflammation, fibrosis, or to promote non-pathogenic tissue repair in the patient.

Figure 8:
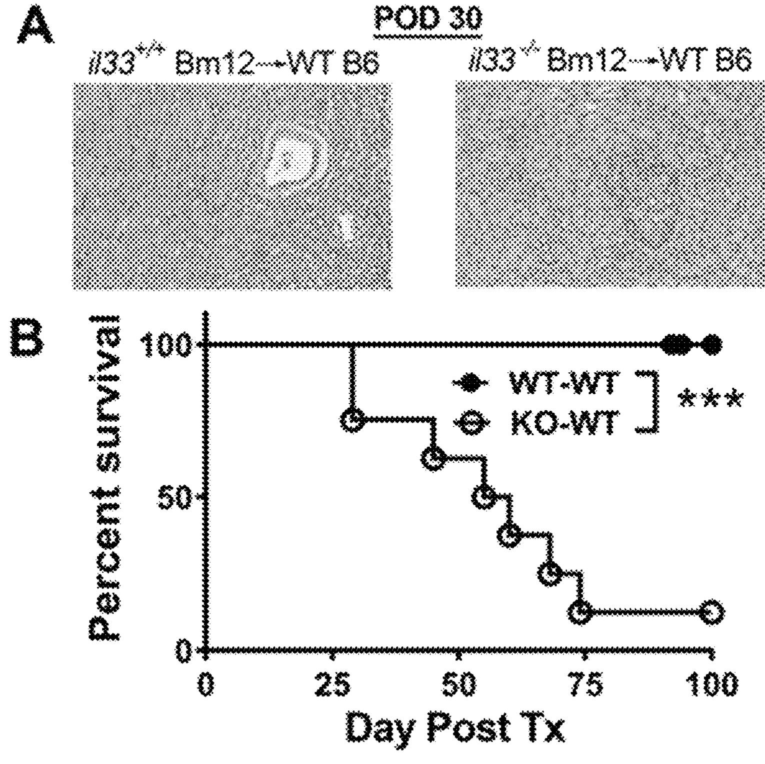
FIGS. 8 and 9. Provide data showing Mice lacking IL-33 are highly susceptible to death after acute lung injury and heart transplants from MHCII mutant (I-A$^{bm12}$) mice lacking IL-33 suffer accelerated chronic rejection (CR) when transplanted into I-A$^b$ recipients (FIG. 8 (A,B)), IL-33 also stimulates both mouse and human (hu) Treg expansion (FIG. 9 (A)) and secretion of IL-13 (FIG. 9 (B)), and that IL-33$^-$ stimulated IL-13 secretion induces Arg1 in macrophages (FIG. 9 (C)).
Figure 9:
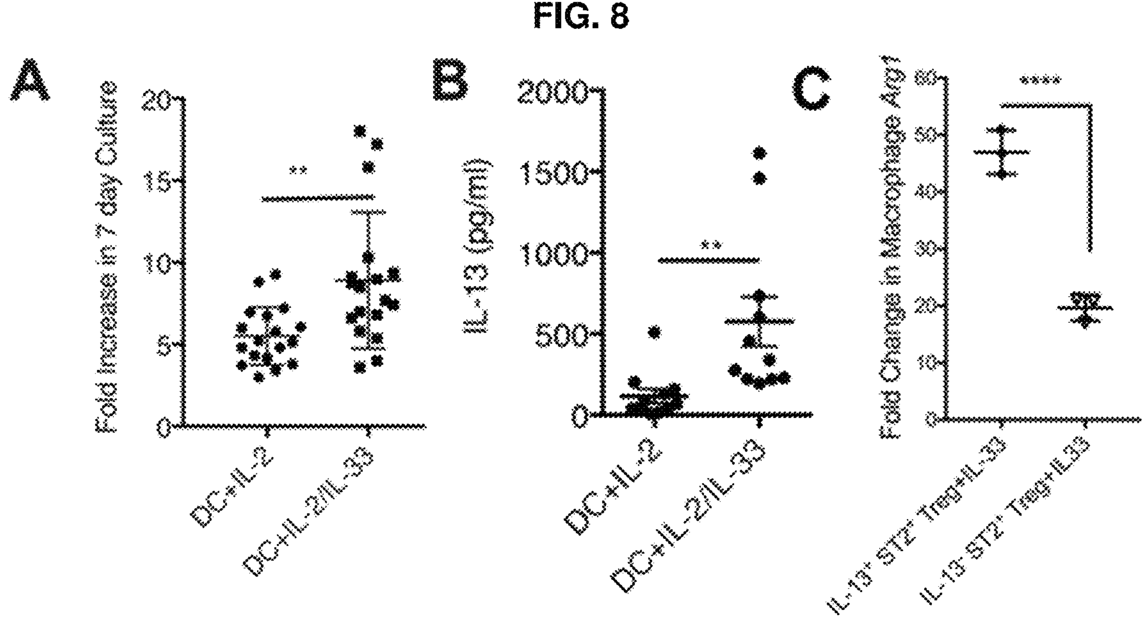

Example 5—Establish Effective MATr Therapy Protocols Preventing CR in Humanized Mice by Combining $IL\text{-}13^+$ Human Treg Cell Therapy and $IL\text{-}33^+$ MBV $IL\text{-}33^-$ stimulated $IL\text{-}13^+$ Treg represent a novel reparative and regulatory immune population: Mice lacking IL-33 are highly susceptible to death after acute lung injury and heart transplants from MHCII mutant ($I\text{-}A^{bm12}$) mice lacking IL-33 suffer accelerated chronic rejection (CR) when transplanted into I-$A^b$ recipients (FIG. 8 (A,B)). IL-33 also stimulates both mouse and human (hu) Treg expansion (FIG. 9 (A)) and secretion of IL-13 (FIG. 9 (B)). Using Treg-specific IL-13 deficient mice, Treg expression of IL-13 does not alter their capacity to suppress other T cell responses, but is required to prevent mortality after acute lung injury. Arginase 1 (Arg1) is an important molecule induced by IL-13 and supports the function regulatory and reparative macrophages. Using Treg and splenic macrophage cultures we used Treg lacking IL-13 to establish that IL-$33^-$ stimulated IL-13 secretion induces Arg1 in macrophages (FIG. 9 (C)). These data suggest that IL-$33^-$ mediated Treg secretion of IL-13, while not important for suppressive function, directs the differentiation of macrophages towards those with reparative or regulatory functions. Tregs prevent autoimmunity by suppressing the immune responses of other T cells, and suppressive Treg cell therapy has been highly effective at thwarting anti-donor immune responses in mice. Yet, recent clinical trials aiming to suppress recipient T cell anti-donor responses have failed to make a significant impact (Koyama I, Bahuda H, K U, Seino K, Habu S, Nakajima I, Fuchinoue S, O'kumura K, Teraoka S. A Clinical Trial with Adoptive Transfer of Ex Vivo-induced, Donor-specific Immune-regulatory Cells in Kidney Transplantation—A Second Report. Transplantation. 2020 November; 104(11):2415-2423 and Sanchez-Fueyo A, et al., Applicability, safety, and biological activity of regulatory T cell therapy in liver transplantation. *Am J Transplant.* 2020 April; 20(4):1125-1136). Although suppressive Treg clinical trials have been unsuccessful, infused IL-13-secreting Treg may be highly effective in improving solid organ transplant (SOTx) outcomes by generating reparative and regulatory macrophages that support tissue repair and local regulation in the graft.

Figure 10:
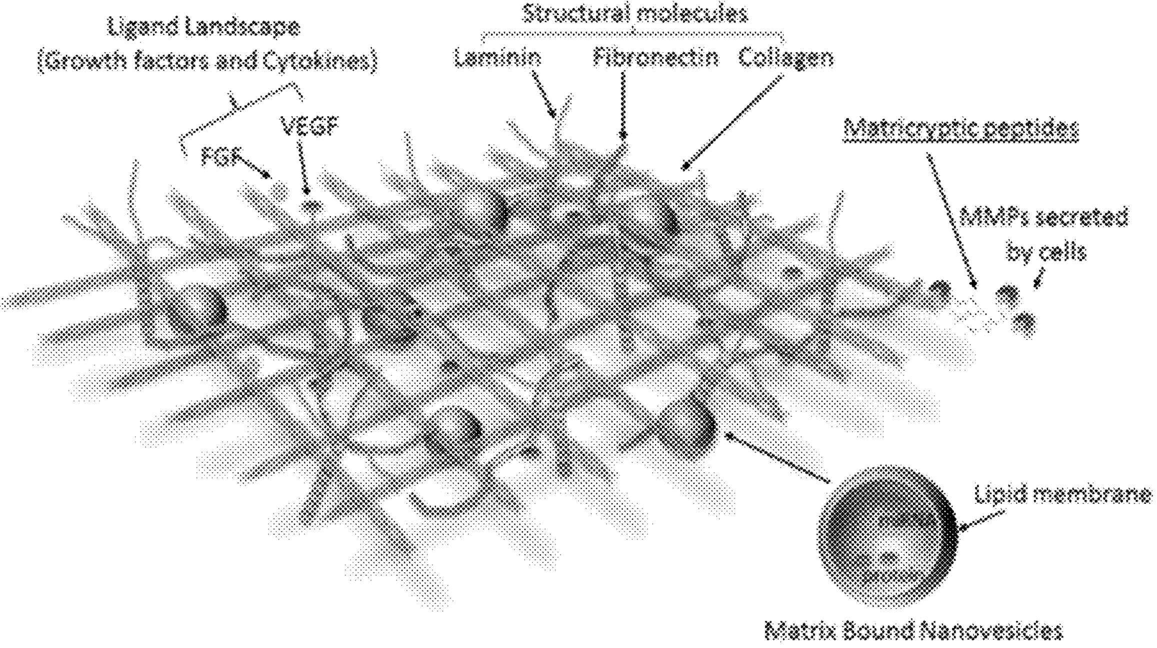
FIG. 10 provides a schematic illustration of MBVs in ECM.
Figure 11:
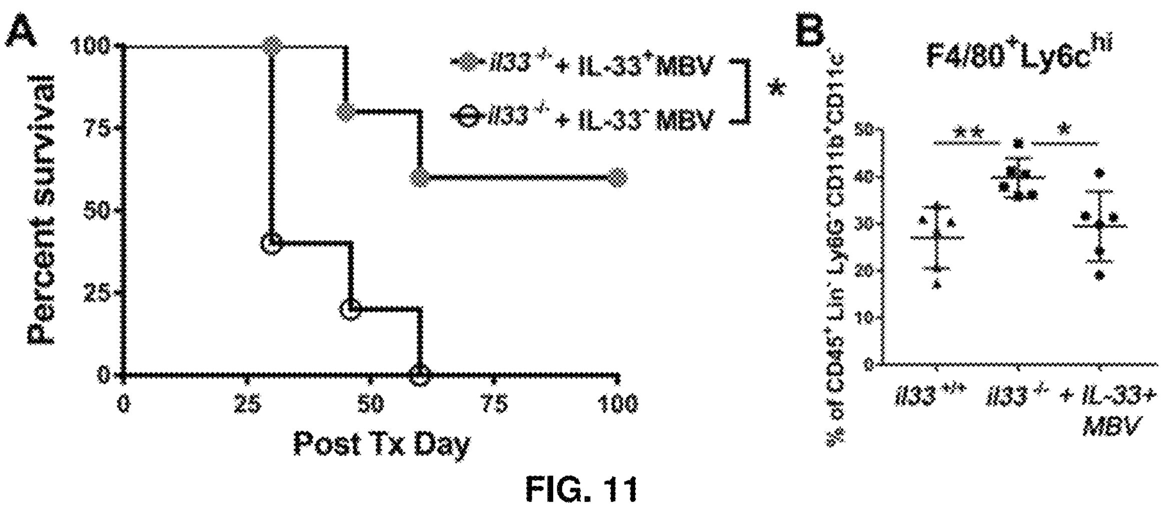
FIG. 11 provides graphs showing that, when delivered at the time of transplant, IL-33$^+$ MBV, but not IL-33$^-$ MBV limits late loss of heart transplants due to CR (A) by blocking the early generation of Ly6c$^{hi}$ pro-inflammatory macrophages in the graft (B).

IL-$33^+$ MBV show promise to limits CR after SOTx: MBV are a distinct class of nanometer-sized (~50-200 nm diameter), lipid membrane vesicles that are bound within the collagen network of the ECM (Hussey G S, Pineda Molina C, Cramer M C, Tyurina Y Y, Tyurin V A, Lee Y C, El-Mossier S O, Murdock M H, Timashev P S, Kagan V E, Badylak S F. Lipidomics and RNA sequencing reveal a novel subpopulation of nanovesicle within extracellular matrix biomaterials. Sci Adv. 2020; 6(12):eaay4361 and Huleihel L, Hussey G S, Naranjo J D, Zhang L, Dziki J L, Turner N J, Stolz D B, Badylak S F. Matrix-bound nanovesicles within ECM bioscaffolds (see, e.g., FIG. 10). Science Advances. 2016; 2(6):e1600502). We have shown that MBV alone can recapitulate the ability of ECM to promote a pro-remodeling macrophage phenotype (Huleihel L, Dziki J L, Bartolacci J G, Rausch T, Scarritt M E, Cramer M C, Vorobyov T, LoPresti S T, Swineheart I T, White L J, editors. Macrophage phenotype in response to ECM bioscaffolds. Seminars in immunology; 2017: Elsevier and Huleihel L, Bartolacci J, Dziki J L, Vorobyov T, Arnold B, Scarritt M, Pineda Molina C, LoPresti S, Brown B, Badylak S F. Matrix bound nanovesicles recapitulate extracellular matrix effects on macrophage phenotype. Tissue engineering Part A. 2017). Moreover, we recently reported that MBV are a rich and stable source of IL-33 that directs macrophages towards a reparative phenotype in vitro (Hussey G S, Dziki J L, Lee Y C, Bartolacci J G, Behun M, Turnquist H R, Badylak S F. Matrix bound nanovesicle-associated IL-33 activates a pro-remodeling macrophage phenotype via a non-canonical, ST2-independent pathway. *J Immunol Regen Med.* 2019; 3:26-35). Our new data suggest that delivered IL-33, in addition to expanding Treg, can directly modulate local macrophages. When delivered at the time of transplant, IL-$33^+$ MBV, but not IL-$33^-$ MBV limits late loss of heart transplants due to CR (FIG. 11 (A)) by blocking the early generation of Ly6$c^{hi}$ pro-inflammatory macrophages in the graft (FIG. 11 (B)).

In view of the above, it is believed that reparative IL-$13^+$ Treg and IL-$33^+$ MBV alone, or together as MATr therapy, will be highly effective when delivered in connection with clinical SOTx to limit early graft damage caused by reprograming infiltrating pro-inflammatory myeloid cells that typically initiate early alloimmune responses after ischemic injury into reparative and regulatory macrophages that resolve inflammation and carry out tissue repair to prevent CR-associated vasculopathy. This approach would represent a first-in-class, microparticle augmented adoptive cell therapy.

B6 $Rag2^{-/-}$ $il2rg^{-/-}$ mice (n=6/group) may have a section of human coronary artery (CAD) obtained from hearts deemed not suitable for SOTx grafted into the abdominal aorta as described in Nadig et al. (Nadig S N, Wieckiewicz J, Wu D C, Warnecke G, Zhang W, Luo S, Schiopu A, Taggart D P, Wood K J. In vivo prevention of transplant arteriosclerosis by ex vivo-expanded human regulatory T cells. *Nat Med.* 2010; 16(7):809-13). Before Tx, CAD grafts may be (a) perfused with cold preservation solution or (b) coated with hydrogels alone or containing escalating doses of MBV, e.g., ranging from $10^5$ to $10^{12}$ particles, and increments there between. A day later non-CR control mice (Grp 1) may receive $1\times10^7$ autologous (from the CAD donor) PBMC or allogeneic PBMC to induce CR (Grp2). Acute rejection is not anticipated and CR assessments based on histological assessment of vasculopathy and fibrosis may be completed at d30. We also may use immunofluorescence-based confocal microscopy of tissues and/or flow cytometry-based assessment of isolated immune cells to define how treatments altered human ($HLA^+$) T, B, and myeloid cells phenotype in the secondary lymphoid tissues and CAD grafts. Particular focus may be on alterations in the pro-inflammatory vs. regulatory/reparative macrophages.

Figure 12:
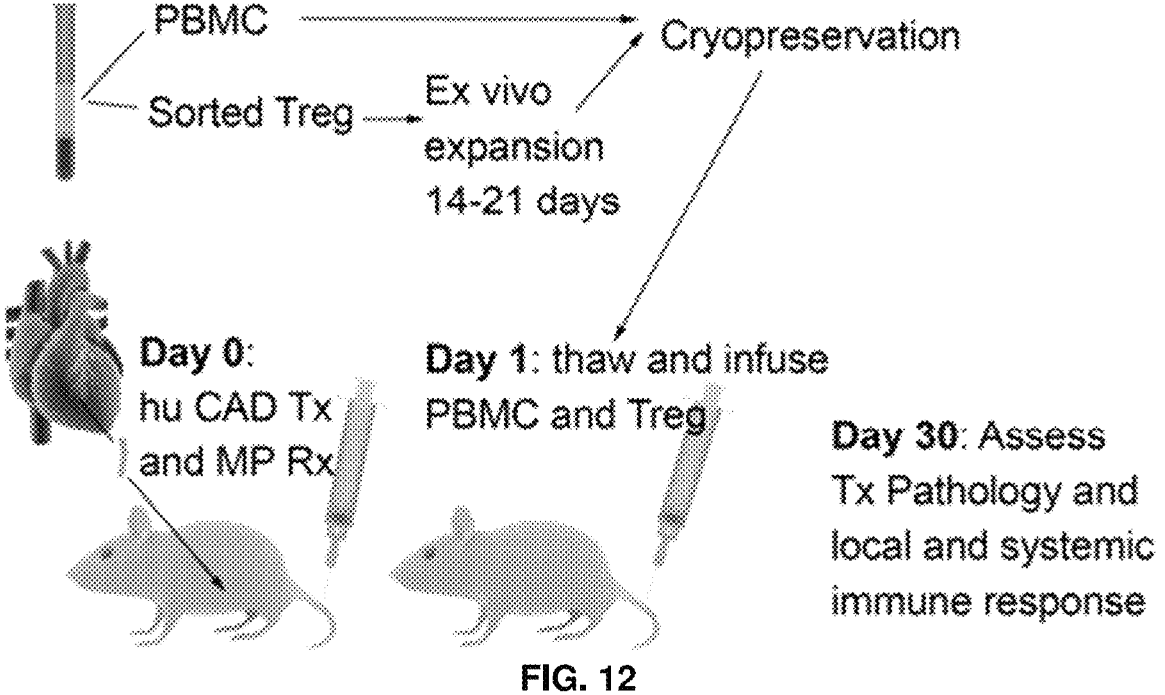
FIG. 12 depicts schematically a method outline establishing clinically applicable expansion protocols for reparative Treg and testing MATr Therapy.

A clinically-feasible and scalable protocol is developed for generation of human reparative Treg. IL-2-expanded human Treg cells can be generated from the recipient prior to transplant surgery, and cryopreserved for later use (See, e.g., Nadig et al.). The expansion protocols for reparative Treg are verified to determine if they are clinically applicable (See, e.g., FIG. 12). To this end, we can establish that adequate numbers of IL-13-secreting Treg are generated for therapy using mDC or artificial APCs that expanded Treg can retain their viability and function (Teff suppression, secretion of IL-10 and IL-13) after cryopreservation. Specifically, in these studies, we may compare the yield and function of expanded Treg before and after cryopreservation. Treg may be expanded from $CD4^+$ $CD25^{hi}$ $CD127^{lo}$ cells sorted from PBMC obtained from Leukopacks (Vitalant-Central Blood Bank) cultured with 1) recombinant human IL-2 (300 U/ml) alone, or 2) with recombinant human IL-33 (50 ng/ml) and a) mDC, e.g., as above, or b) L-32 cells, e.g., as above, which are fibroblasts modified to act as artificial APC through engineering to provide TCR and CD28 stimulation, as well as CD2 binding (Sasaki K, Wang Y C, Lu L, Hughes J, Vujevich V, Thomson A W, Ezzelarab M B. Combined GM-CSF and G-CSF administration mobilizes CD4(+) CD25(hi) Foxp3(hi) Treg in leukapheresis products of rhesus monkeys. *Am J Transplant.* 2019).

B6 $Rag2^{-/-}$ $il2rg^{-/-}$ mice (n=6/group) have a section of human coronary artery (CAD) obtained from hearts deemed not suitable for Tx grafted into the abdominal aorta, e.g., as described above. A day later mice may receive $1\times10^7$ of 1) autologous (from the CAD donor) or 2) allogeneic PBMC alone, or with $1\times10^7$ Treg expanded from the same allogeneic PBMC using a) IL-2, or b) IL-2 and IL-33, e.g., as defined most effective above. Before Tx, CAD may be infused with or coated with hydrogels containing MPV in the most effective method, e.g., as determined above. As above, acute rejection is not anticipated and CR assessments based on histological assessment of vasculopathy and fibrosis may be completed at d30. We also may use immunofluorescence-based confocal microscopy of tissues and/or flow cytometry-based assessment of isolated immune cells to define how treatments altered human (HLA$^+$) T, B, and myeloid cells phenotype in the secondary lymphoid tissues and CAD grafts. Particular focus may be on alterations in the pro-inflammatory vs. regulatory/reparative macrophages.

If we see prevented CR, as expected, mechanistic studies may be completed at early time points to confirm beneficial early modulation of graft myeloid cells. This humanized mouse model may be conducive to follow up studies to assess how MATr Therapy works with currently immunosuppressives and guide the next step of non-human studies, and then rapid progression to clinical trials.

Although non-limiting embodiments have been described in detail for the purpose of illustration, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed:

1. A method of treating a patient having an injury or inflammatory condition, comprising parenterally administering to the patient an amount of ex vivo-expanded regulatory T cells (Treg cells) effective to reduce inflammation in the patient, wherein the Treg cells are activated to produce IL-13$^+$ by IL-33$^+$ matrix-bound vesicles (IL-33$^+$ MBVs), wherein the Treg cells are activated by ex vivo co-culture with the IL-33$^+$ MBVs prior to administration to the patient.

2. The method of claim 1, wherein the IL-33+ MBVs are autologous, syngeneic, allogeneic, or xenogeneic to the patient and/or the Treg cells are autologous to the patient.

3. The method of claim 1, wherein the ex vivo-expanded Treg cells are expanded in culture medium comprising IL-33, and express and/or secrete IL-13, and optionally have the phenotype CD4$^+$CD25$^{hi}$Foxp3$^{hi}$IL-13$^+$.

4. The method of claim 1, wherein the Tregs are administered locally, to a site of injury or inflammation in the patient, intravenously to the patient, or intraperitoneally to the patient.

5. The method of claim 1, wherein the patient has a systemic inflammatory response syndrome (SIRS).

6. The method of claim 5, wherein the patient has a SARS-CoV2 infection or a myocardial infarct.

7. The method of claim 1, wherein the injury or inflammatory condition is a graft rejection.

8. The method of claim 7, wherein the Treg cells are perfused into the graft.

* * * * *

SEQUENCE LISTING

```
<160> NUMBER OF SEQ ID NOS: 3

<210> SEQ ID NO 1
<211> LENGTH: 88
<212> TYPE: RNA
<213> ORGANISM: Homo sapiens

<400> SEQUENCE: 1

caccuugucc ucacggucca guuuucccag gaaucccuua gaugcuaaga uggggauucc     60

uggaaauacu guucuugagg ucaugguu                                        88


<210> SEQ ID NO 2
<211> LENGTH: 110
<212> TYPE: RNA
<213> ORGANISM: Homo sapiens

<400> SEQUENCE: 2

agaagggcua ucaggccagc cuucagagga cucccaaggaa cauucaacgc ugucggugag     60

uuugggauuu gaaaaaacca cugaccguug acuguaccuu gggguccuua               110


<210> SEQ ID NO 3
<211> LENGTH: 106
<212> TYPE: RNA
<213> ORGANISM: Homo sapiens

<400> SEQUENCE: 3

gcgcagcgcc cugucuccca gccugaggug cagugcugca ucucugguca guugggaguc     60

ugagaugaag cacuguagcu caggaagaga gaaguuguuc ugcagc                   106
```